(12) United States Patent
Palmer

(10) Patent No.: US 12,082,937 B2
(45) Date of Patent: Sep. 10, 2024

(54) SYSTEM AND METHOD FOR TASTE PREFERENCE TESTING AND ASSESSMENT

(71) Applicant: OPERTECH BIO, INC., Philadelphia, PA (US)

(72) Inventor: R. Kyle Palmer, Cranbury, NJ (US)

(73) Assignee: OPERTECH BIO, INC., Philadelphia, PA (US)

( * ) Notice: Subject to any disclaimer, the term of this patent is extended or adjusted under 35 U.S.C. 154(b) by 968 days.

(21) Appl. No.: 16/980,206

(22) PCT Filed: Mar. 13, 2019

(86) PCT No.: PCT/US2019/022059
§ 371 (c)(1),
(2) Date: Sep. 11, 2020

(87) PCT Pub. No.: WO2019/178233
PCT Pub. Date: Sep. 19, 2019

(65) Prior Publication Data
US 2021/0022658 A1    Jan. 28, 2021

Related U.S. Application Data

(60) Provisional application No. 62/642,195, filed on Mar. 13, 2018.

(51) Int. Cl.
*A61B 5/00*    (2006.01)
(52) U.S. Cl.
CPC ................... *A61B 5/4017* (2013.01)

(58) Field of Classification Search
None
See application file for complete search history.

(56) References Cited

U.S. PATENT DOCUMENTS

| | | | |
|---|---|---|---|
| 6,876,973 B1* | 4/2005 | Visconti | G06Q 10/02 |
| | | | 705/5 |
| 8,364,520 B1 | 1/2013 | Eichorn et al. | |
| 8,504,440 B1* | 8/2013 | Kolawa | G06Q 30/00 |
| | | | 705/26.7 |
| 9,841,897 B2 | 12/2017 | Palmer et al. | |
| 2002/0094359 A1 | 7/2002 | Prosise et al. | |
| 2013/0030951 A1* | 1/2013 | Nicod | G06Q 30/02 |
| | | | 705/26.7 |
| 2014/0143020 A1 | 5/2014 | Wolfe et al. | |

(Continued)

FOREIGN PATENT DOCUMENTS

WO    WO-2015021281 A2 *    2/2015    ........... A61B 5/4017

*Primary Examiner* — Romain Jeanty
(74) *Attorney, Agent, or Firm* — Casimir Jones, S.C.; Brian F. Bradley

(57) ABSTRACT

The present invention provides systems and methods for testing and assessing preference (e.g., taste preference). In one aspect, various aspects of an individuals taste preferences (e.g., degree an individual likes/dislikes a taste ingredient, degree an individual is willing to pay to keep/exclude a taste ingredient) are tested and assessed. In a further aspect, the taste preferences of a plurality of individuals are tested, assessed, and compared and, optionally, individuals are rewarded for their taste preference(s). Apparatus, computer readable media and systems for implementing the taste preference assessment and provision of rewards are also provided.

11 Claims, 14 Drawing Sheets

(56) References Cited

U.S. PATENT DOCUMENTS

| | | | |
|---|---|---|---|
| 2014/0278990 A1* | 9/2014 | Swanson | G06Q 30/0207 |
| | | | 705/14.55 |
| 2015/0186971 A1* | 7/2015 | Holman | G07F 9/001 |
| | | | 705/15 |
| 2016/0154581 A1 | 6/2016 | Palmer et al. | |
| 2016/0171514 A1* | 6/2016 | Frank | G06Q 30/02 |
| | | | 705/7.29 |
| 2018/0025386 A1* | 1/2018 | Lee | G16H 10/60 |
| | | | 705/14.66 |

* cited by examiner

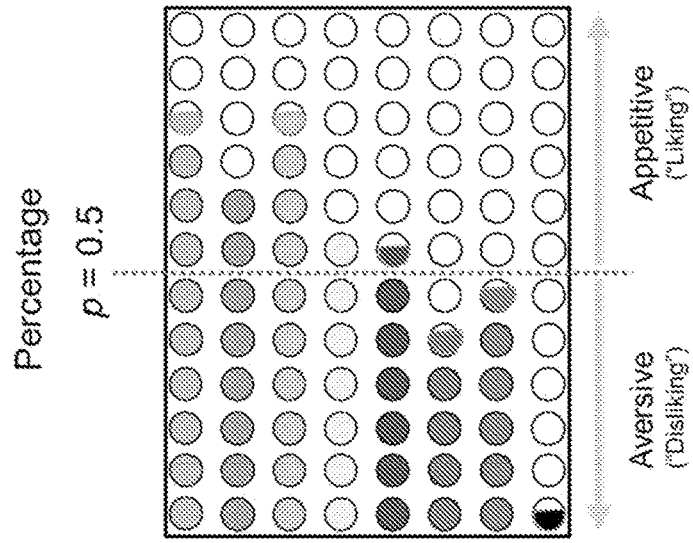
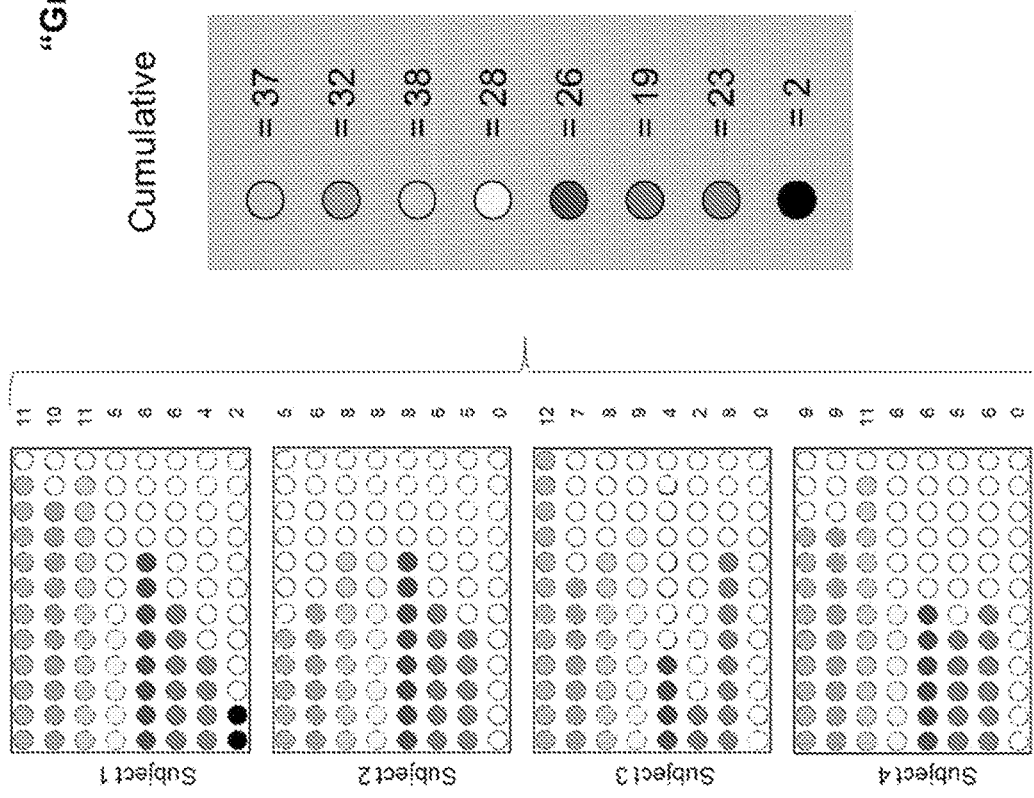
FIG. 5

Configuration of 96 well plate

Plate A
1. Citric Acid (10mM)
2. NaCl (100 mM)
3. Quinine (0.5 mM)
4. Sucrose (500 mM)
5. Sucrose (250 mM)
6. Sucrose (200 mM)
7. Sucrose (125 mM)
8. Sucrose (62.5 mM)
9. Sucrose (31.25 mM)
10. Sucrose (200 mM) + Quinine (0.5 mM)
11. Sucrose (200 mM) + Quinine (0.125 mM)
12. Water

Plate B
1. Citric Acid (10mM)
2. NaCl (100 mM)
3. Quinine (0.5 mM)
4. Rebaudioside A (1 mM)
5. Rebaudioside A (0.5 mM)
6. Rebaudioside A (0.25 mM)
7. Rebaudioside A (0.125 mM)
8. Rebaudioside A (0.0625 mM)
9. Sucrose (200 mM)
10. Sucrose (200 mM) + Quinine (0.5 mM)
11. Sucrose (200 mM) + Quinine (0.125 mM)
12. Water

Plate C
1. Citric Acid (10mM)
2. Glutamic acid (10 mM) + sucrose (100 mM)
3. Glutamic acid (10 mM) + sucrose (300 mM)
4. Glutamic acid (10 mM) + sucrose (500 mM)
5. Glutamic acid (10 mM)
6. NaCl (100 mM)
7. Quinine (0.5 mM) + sucrose (300 mM)
8. Quinine 0.5 mM
9. Sucrose (100 mM)
10. Sucrose (300 mM)
11. Sucrose (500 mM)
12. Water

FIG. 6B

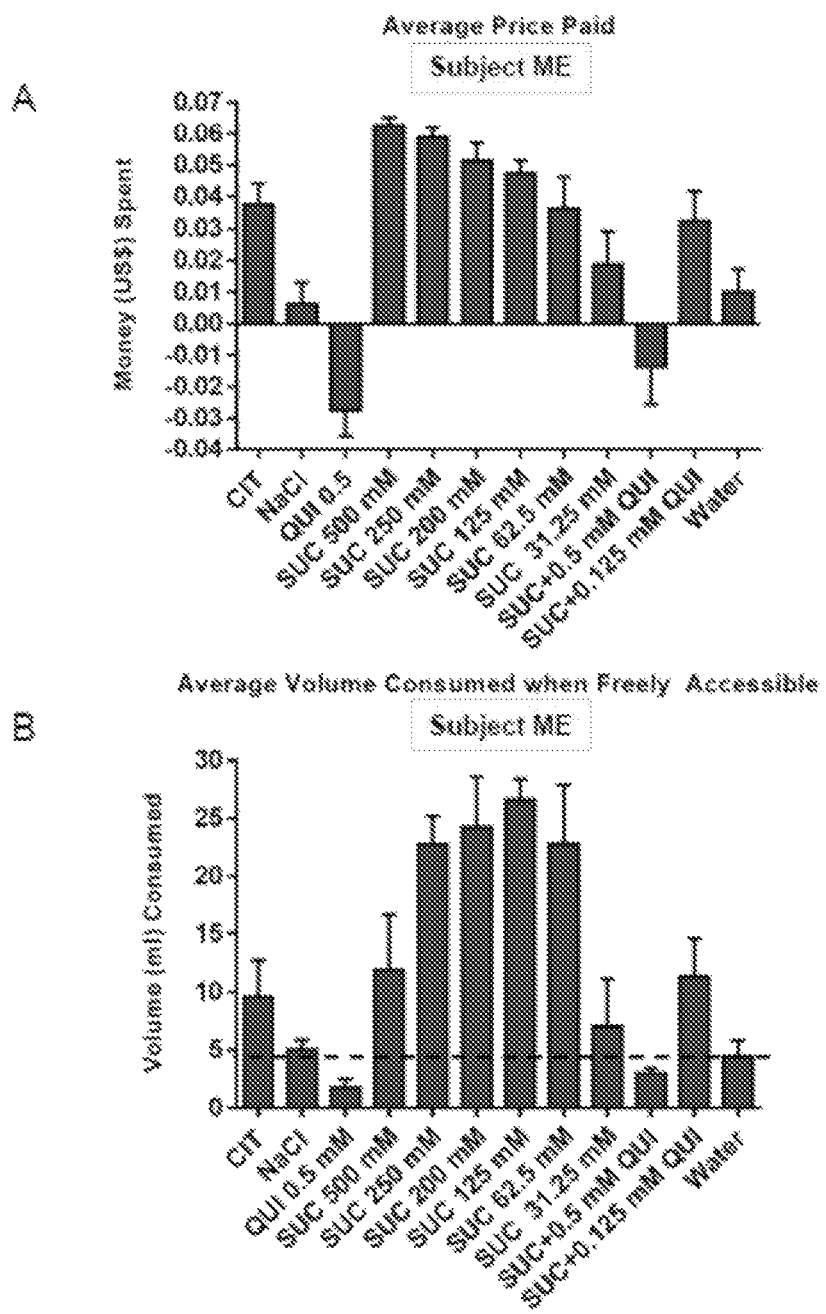

SYSTEM AND METHOD FOR TASTE PREFERENCE TESTING AND ASSESSMENT

FIELD

Provided herein are systems and methods for testing and assessing taste preference. In one aspect, various aspects of an individual's taste preferences (e.g., degree an individual likes/dislikes a taste ingredient, degree an individual is willing to pay to keep/exclude a taste ingredient) are tested and assessed. In a further aspect, the taste preferences of a plurality of individuals are tested, assessed, and compared and, optionally, individuals are rewarded for their taste preference(s). Apparatus, computer-readable media and systems for implementing the taste preference assessment and provision of rewards are also provided.

BACKGROUND

When designing a product, or conducting market research, it is useful to gain an accurate and objective measure of the qualitative and/or quantitative reactions of an individual (e.g., a human subject) to a given product. For example, human taste testing is performed to obtain a measure of taste quality and/or palatability of test samples (e.g., foods, beverages, pharmaceuticals, nutraceuticals, etc.). Human taste testing typically requires large amounts of sample and large numbers of trained subjects in order to generate statistically relevant data. Testing conventionally uses 20-40 or more test subjects (e.g., human subjects) per test panel with each subject evaluating (e.g., consuming) a large amount of sample per analysis (e.g., 20, 30, 40 or more milliliters of sample solution). Therefore, generation of a working/testable amount of test sample needed for evaluation has remained a significant challenge. For example, a taste-active compound/ingredient that is active in the mM range might need to be scaled to 10-100s of grams for testing, which can be very costly, especially if the test article is a natural product. Human taste testing therefore remains time and resource intensive. Furthermore, due to predominant reliance on subjective verbal reports or rating scales for test measurement, human taste testing has been notoriously variable and inaccurate. Similar inefficiencies and inaccuracies exist for other types of human assessment testing as well.

Moreover, human taste testing has stagnated into a structure of testing and measurement that progressed from psychophysical methods originating over 100 years ago with little innovation since.

SUMMARY

The disclosure of the present invention satisfies the foregoing needs by providing, inter alia, systems and methods for identifying, evaluating and utilizing assessed taste preferences. In one aspect, systems and methods associated with identifying and/or learning taste preference assessment are disclosed. In one embodiment, the method includes providing one or a plurality of subjects and a taste preference system, where the taste preference system comprises one or more of an initial sum of goods to be used (e.g., spent, traded or the like) by the subject (e.g., a pot of money, number of goods, or other set of items that provide value to the subject); a plurality of taste samples (e.g., one or a plurality of ingredients) to be tasted by the subject; means for the subject to record the subject's decision to accept/retain or reject/exclude a taste sample from the plurality of taste samples; means for the subject to identify and record a value of a portion of the sum of goods with the decision to accept/retain or reject/exclude the taste sample from the plurality of samples; means for comparing taste samples retained or excluded by a subject with either a control or with other subjects; and/or means for compensating a subject (e.g., based upon samples retained or excluded). The invention is not limited by the initial sum of goods to be used (e.g., to associate a value with a decision to keep or to reject a taste sample) by the subject. A non-limiting example of a sum of goods is a sum of money. Any sum of goods that can be used by a subject to buy, trade, invest, risk, or the like may be used (e.g., for a subject to associate a value (e.g., a percent value) of the sum of goods) with a decision to keep or to reject a taste sample. In some embodiment, the total of the sum of goods is shared (e.g., in equal or non-equal parts) among a set number of subjects (e.g., a set number of subjects being assessed for taste preference). The invention is not limited by the type of taste sample. Indeed, a taste sample may contain one or a plurality of ingredients. Similarly, a taste sample may contain one or a plurality of samples (e.g., each containing one or a plurality of ingredients). Ingredients may be, but are not limited to, ingredients categorized according to "basic tastes" (and combinations of same) such as sweet (e.g., nutritive, non-nutritive, natural product sweeteners), salty (e.g., sodium chloride, salt-substitutes (e.g., potassium chloride) or mixtures of same), sour (e.g., citric acid, ascorbic acid (vitamin C), acetic acid (vinegar), phosphoric acid (e.g., "acidulant" used in soft drinks), and any organic or inorganic acids mixed with other taste stimuli (such as sweeteners) or ingredients to create complex tastes), umami (e.g., monosodium glutamate, potassium glutamate, other "umami" amino acids, broth (e.g., beef, chicken, fish, vegetable) or mixtures of any or all of same), and bitter (e.g., bitter flavors such as quinine, absinthe, hops and hop-teas, cocoa, chicory, caffeine, naringen, and citrus zest, as well as pharmaceuticals such as diphenhydramine, guaifenesin, cetirizine, dextromethorphan, metronidazole, asenapine, prednisolone, and progesterone). Ingredients also may be chemesthetics such as capsaicin, menthol, spearmint, mustard oil (allyl isothiocynate), curcumin, various spices, and thymol. Additional ingredients include, but are not limited to, flavors such as berry, lemon, tomato, banana, etc. Other examples of ingredients include excipients, such as those used in pharmaceutical formulations, for example, maltose, cyclodextrin, gelatin, polyethylene glycol, and hydroxypropyl methylcellulose. A taste sample may include a single ingredient, or any combination of ingredients (e.g., combined pair-wise exhaustively, or in pairs, triplets, quadruplets, etc. using a combinatorial approach). The invention is not limited by the amount of taste sample tested by a subject. In some embodiments, a taste sample is sampled in a volume of between 0.1-1.0 ml, although smaller (e.g., 0.001-0.1 ml) or larger (1.0-100 ml or greater) volumes may be used/sampled. Taste samples may be tested/presented randomly, or in other embodiments, tested/presented in a specific order (e.g., to determine the effect of presentation order on preference). The invention is not limited by the means for the subject to record the subject's decision to accept/retain or reject/exclude a taste sample (e.g., from the plurality of taste samples). Indeed, any means for recording a subject's determination (e.g., like/keep or dislike/exclude) regarding a taste sample may be used. A non-limiting example of a means to record a subject's determination is a touch screen configured with choices (e.g., reject or accept) that is connected to a computer, such that when the subject presses the touch screen the subject's choice regarding the taste sample is recorded in a memory component of the computer. The invention is also not limited by the means for the subject to identify and record a value of a portion of the sum of goods with the decision to accept/retain or reject/exclude the taste sample from the plurality of samples. Indeed, any means for the subject to identify and record a value of a portion of the sum of goods with the decision (e.g., to reject or accept) regarding the taste sample from the plurality of samples may be used. In one non-limiting example, the system includes a sliding scale selection tool that allows a subject to place a value on the subject's decision (e.g., to reject or accept) regarding the taste sample. The invention is not limited by the type of sliding scale. In one embodiment, a subject moves the bar to place the probability of inclusion/exclusion (e.g., the bar indicates the probability to nearest $100^{th}$ and the cost of the decision is adjusted as the bar moves). For example, in one embodiment, when a subject is making a determination to keep or exclude a taste sample, the subject adjusts the scale thereby associating the cost (e.g., a portion of the value of the subject's sum of goods (e.g., money)) of executing the choice (e.g., like/keep or dislike/exclude) with the probability of outcome for the choice (e.g., the more value (e.g., money) the subject is willing to spend to keep or exclude the sample, the higher the probability will be that the taste sample is kept or excluded. The invention is not limited by the means for comparing taste samples retained or excluded by a subject (e.g., with taste samples retained/excluded by other subjects). For example, in one embodiment, taste sample data (e.g., data sets generated via a subject's decisions to keep or exclude a taste sample) are categorized according to taste quality and/or palatability. In another embodiment, taste sample data (e.g., data sets generated via a subject's decisions to keep or exclude a taste sample) are categorized according to the value spent by a subject to keep or exclude a taste sample (e.g., via the probability distribution of the sliding scale). The invention is not limited by the means for compensating a subject that uses a system or method described herein (e.g., to analyze taste preference based upon samples retained or excluded). In one embodiment, a subject creates a set (e.g., a plate) of retained taste samples (e.g., determined by the price the subject is willing to pay to keep and/or exclude taste samples), and upon completing creation of the set of samples, the set (e.g., plate of samples) is judged (e.g., by demand of other subjects (e.g., a market), such that the more favorably a completed set is judged, the higher the demand and resulting value). In a further embodiment, a subject spends a portion (e.g., ranging from anywhere between 1-99%) of their initial sum of goods (e.g., money) to generate a preferred (e.g., evidenced by the subject's willingness to expend funds to retain and/or exclude a sample) set of retained samples that the subject believes other subjects (e.g., a marketplace) will also find preferable/liked. In some embodiments, a subject will spend less on a set of samples that, overall, the subject finds less appealing, and therefore will retain more of the initial sum of goods (e.g., money) than in a scenario where the subject finds a set of samples more appealing and therefore willing to spend more. In a further embodiment, a subject is rewarded (e.g., a subject receives goods (e.g., money)) by the market if the subject's plate contains samples that are highly palatable and excludes samples that are unpalatable (e.g., the amount of money reward is significantly greater (e.g., 10 times greater) if the market likes the plate of retained samples than if the subject had spent no money. A market reward can be based on a number of factors and or algorithms, including, but not limited to, those described herein. In one embodiment, a subject keeps the value of what is left of the original sum value (e.g., original pot of money). In another embodiment, a subject is also compensated for the subject's contribution to the composition of a "Grand Collective Plate (e.g., a plate of most preferred samples). The invention is not limited by the method of testing subject's impact on performance. A calculation can be performed giving a percentage similarity between subject's plate and Grand Collective plate. Compensation can be scaled according to the percent identity.

In another aspect, a system associated with taste preference assessment is enabled to provide objective taste preference identification and/or evaluation in a game-like setting. For example, in one embodiment, a system containing taste samples randomly selects the samples from a plate of samples (e.g., via an automated component (e.g., an automated robotic arm and/or pipette)), makes the samples individually available to a subject for testing, prompts a subject (e.g., via computer screen/monitor) to make a choice to retain or exclude (e.g., based upon like or dislike, respectively) a sample, upon making a choice, provides the subject the ability to weigh the value of making the choice to retain or exclude (e.g., via providing a cost of execution presentation (e.g., via computer screen/monitor) that a subject adjusts to scale associating the cost of executing the choice with the probability of outcome for the choice, and, once entered into the system (e.g., via a subject entering the value of the cost execution), records the subject's choice, the value for the choice (e.g., the subject's initial sum of money is reduced accordingly) and identifies the sample retained or excluded (e.g., in a memory component of the system). In one embodiment, once a sample is individually made available to a subject for testing, the subject self-administers the sample for taste testing. In another embodiment, a system visual display is a computer screen or monitor. In a further embodiment, the visual display updates the plate contents on each taste sample test/trial. In some embodiments, a previously retained sample may disappear (on a probabilistic basis) from the subject's retained sample set (e.g., plate) if the price that was paid for inclusion was not high enough relative to other samples. The system, in some embodiments, will repeat the taste sample administration and recording until all taste samples in a set are completed at which time the system indicates an end of testing portion of the game. In some embodiments, after testing, the system will display on the screen/monitor that the game has entered a Market Evaluation portion of the game. Visual stimuli suggesting progress of market analysis may be used (e.g., to keep the subject engaged until the market reward is determined). The invention is not limited by the visual stimuli or information conveyed at this stage. In some embodiments, a timer is displayed. In other embodiments, virtual market activity is displayed indicating real-time bidding (whether based on actual events or simulated by the computer). In further embodiments, ticker prices like a stock market readout or a slot machine are displayed. In still further embodiments, virtual bidders and/or bidding activity is shown in an auction for plates (one of which will be identified as the subject's). In one embodiment, upon completion of the Market Evaluation stage, the system will display the price offered to the subject by the market. In a further embodiment, the subject is paid the remainder of the original pot and the Market Value reward.

In another aspect, a non-transitory computer-readable storage medium having a computer program stored thereon is disclosed. In one embodiment, the computer program includes one or more instructions, which when executed by a processing apparatus (e.g., a computer processor), provides for learning taste preference assessment (e.g., of the systems and methods disclosed herein). In a first variant, the computer program includes one or more instructions, which when executed by a processing apparatus, provide the means for presenting taste samples to a subject and recording a subject's preference to the samples using the systems and methods described.

In still another aspect, systems and methods described herein are used in or as a game (e.g., for one or a plurality of subjects) to identify a taste profile (e.g., of one or a plurality of samples). In one embodiment, taste preferences of one or more subjects are used to generate a taste profile for a taste sample or plurality of taste samples (e.g., how much a particular sample is liked/disliked). For example, in one embodiment, for each round or trial of a game a subject is tasked with generating a plate of taste samples from a plurality of taste samples that the subject identifies as good/pleasant tasting, and starting with an initial sum of goods (e.g., a pot of money), the subject tastes a sample (e.g., from a population of taste samples being tested) and the subject makes a determination of whether to keep or not keep a taste sample based upon whether the subject likes or dislikes the taste of the sample. For example, if a subject likes a sample the subject will chooses to include the sample (e.g., for generating a plate of retained/kept samples) and if the subject does not like a sample the subject chooses to exclude the sample (e.g., from a plate of retained, liked samples). Choosing to include or exclude a taste sample may be designated using any means. In one embodiment, pressing a touch screen configured with the options to "include" or "exclude" are used by a subject to designate whether the subject wishes to include or exclude a taste sample, and in order to execute the include/exclude command, the subject selects a monetary value associated with a probability of guaranteeing the outcome of the command with the monetary value subtracted from the initial sum of good (e.g., pot of money) when the decision is executed (e.g., using a sliding scale that monetizes based on probability the likelihood of keeping/excluding). In one embodiment, a subject is compensated at the end of a round by how many samples in the subject's plate are common to the cumulative set of samples that are present in the plates of all subjects (e.g., that are participating in the round, or that generated a plate using the same population of taste samples being tested). One or more rounds may be used. In some embodiments, subjects are trained to recognize specific taste properties of samples (e.g., salty, sweet, bitter, sour, umami, neutral (no taste) prior to playing the game). The invention is not limited by the type of taste sample dispensing system. Any system that can obtain a taste sample from a population of taste samples, deliver the sample to a subject, and keep track of the sample and the subject's decision to include or exclude the sample may be used. In some embodiments, the present invention provides a system and/or device for taste testing (e.g., human taste testing) comprising: (a) a touch screen; (b) an automated pipette component; and (c) a sample source. Exemplary systems of taste sample delivery are described herein. In some embodiments, the game includes forming a market by a cohort of multiple subjects that are also evaluating the same set of taste samples/ingredients, with each subject creating his/her own plate. At the end of all rounds/sessions in the cohort, a "Grand Collective Plate" will be derived from all of the samples occurring in each of the subject's final plate. The "Grand Collective Plate" may be comprised of high replicates of samples that were chosen to be included with high probability (i.e., that subjects paid a premium to include), decreasing replicates of samples that subjects paid a lower price to either include or exclude, and few, or no replicates of samples that subjects paid a premium to exclude.

In another aspect, the invention provides multiple types of information/data that is obtainable using the systems and methods described herein. In one embodiment, the data identifies the price paid by each subject/participant for each sample (e.g., a reflection of the individual and/or cumulative value of the sample). In another embodiment, the data identifies the probability that resulted for inclusion/exclusion of each sample (e.g., a reflection of the perceived importance to the individual and/or cumulative subjects of his/her actions). In some embodiments, the data identifies the overall composition of the "Grand Collective Plate" (e.g., as an indication of the generalizability of the results). The data may also include identification of appetitive tastes including, but not limited to, the best tasting among any random set of ingredients, the best tasting among a focused set (e.g., the best in salty class, sweet class, savory class), rank ordering of among ingredients within and across sets, and building a database from all tests for ad hoc analysis across datasets of any kind. Many different types of samples may be tested including, but not limited to, salt substitutes, like potassium chloride, by themselves or in a product, non-nutritive sweeteners, which often have bitter off tastes or are not preferred because of the temporal aspects of the sweet taste sensation (e.g., lingering sweet aftertastes), and complex taste categories, such as savory ('umami")). Mixtures of taste samples/ingredients may also be tested in a game like environment. The data may include identification of aversive tastes including, but not limited to, identification of taste samples with varying degrees of probability of being left out of the plate (e.g., the most aversive taste samples will never, or seldom, be included in a generated plate, and as aversiveness declines, appearance in the plate will increase). Identification of aversive taste samples finds particular benefit for pharmaceutical formulations. For example, using the systems and methods of the invention it is possible to tie taste discrimination results (e.g., from a screen of bitter blockers) to acceptability (preference). Such data finds use in situations or environments where the aversive taste of the active pharmaceutical ingredient (API) is not itself ameliorated (e.g., bitter blocking per se has not been effective) but the taste of the vehicle has been formulated to improve overall acceptance regardless of the full bitterness imparted by the API. The data may also include identification of novel ingredients of which the taste properties have not been defined. For example, systems and methods described herein can be used to combine taste discrimination (taste quality) and preference (palatability) into one single assay.

The present invention allows for improved accuracy and/or precision of testing, enables measurements to be achieved through objective means (not relying on verbal reports, rating scales, or subjective perceptions), and the accumulation of statistically relevant information from any cohort of subjects (e.g., many hundreds, several hundred, about 100, about 90, about 80, about 70, about 60, about 50, about 40, about 30, about 20, about 15, 14, 13, 12, 11, 10, 9, 8, 7, 6, 5, 4, 3, 2, or 1, or ranges therein) using small amounts of taste sample/ingredient (e.g., 2, 3, 4, 5, 6, 7, 8, 9, 10, 20, 30, 40, 50-70, 70-90, 100 or more fold less than the amount of taste sample/ingredient conventionally used), and/or provides the capability of high throughput testing. In some embodiments, taste samples are of an appropriate size for the particular sample (e.g., 50 µl, 100 µl, 150 µl, 200 µl, 250 µl, 300 µl, 350 µl, 400 µl, 450 µl, 500 µl, 600 µl, 700 µl, 800 µl, 900 μl, 1 ml, 1.5 ml, 2 ml, 2.5 ml, 3 ml, 3.5 ml, 4 ml, 4.5 ml, 5 ml, 6 ml, 7 ml, 8 ml, 9 ml, 10 ml, or more, or ranges or volumes therein).

The invention is not limited by the type of taste testing characteristics measured. Indeed, any and all characteristics related to taste may be measured including, but not limited to, bitter, sweet, salty, umami, sour, watery, etc. Further characteristics may comprise any taste that can result from a constellation of tastes, spicy, minty, cool, metallic, chemesthetic, mouth-feel, appetitiveness, aversiveness, etc.

BRIEF DESCRIPTION OF THE DRAWINGS

FIG. 5 depicts a composite plate (e.g., Grand Collective Plate) derived from four taste test subjects' responses to 8 taste samples/ingredients, each sample presented 12 times in a round. Each of the subject's preferences to the 8 samples/ingredients are translated into a composite (e.g., Grand Collective) plate.

FIG. 9(A) shows price paid on each trial of a given sample to execute the action of "include" or "exclude" in the creation of a customized plate of taste stimulus solutions most "liked" by Subject ME using the TāStation® consumption model game; each of 12 solutions ("Plate A," described in FIG. 6) was presented automatically and randomly in replicates of 8. Positive values on the ordinate indicate the absolute amounts of money spent for inclusion, whereas negative values indicate the absolute amounts of money spent for exclusion. (B) shows the average volumes (out of 30 ml per sample) consumed through a straw by Subject ME when given free access to the samples randomly presented in plastic cups; each of the 12 "Plate A" solutions was dispensed in 3 cups (i.e., total of 36 samples); the cups were given to the subject in a randomized order. The dashed line highlights the average volume per sample of water consumed. CIT=citric acid (10 mM), NaCl=sodium chloride (100 mM), QUI=quinine, SUC=sucrose. Data shown in (A) and (B) were collected on separate days.

DEFINITIONS

Figure 1:
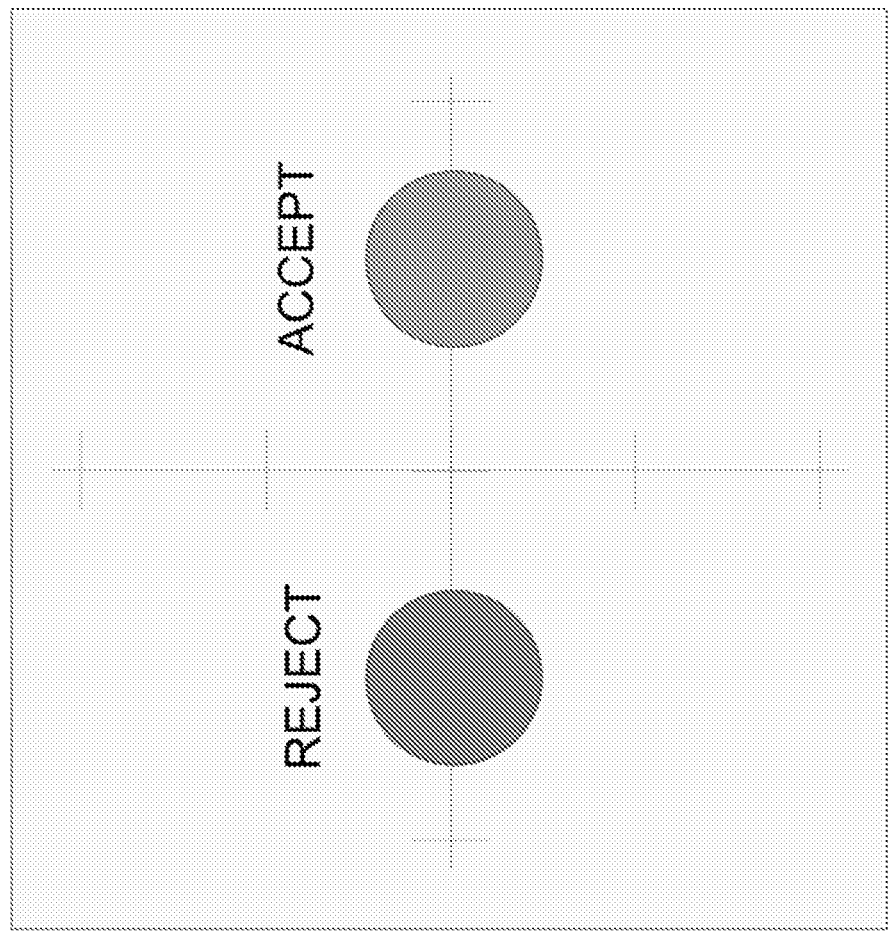
FIG. 1 depicts an exemplary "Choice Screen" used in one embodiment of the invention.

As used herein, the term "operant conditioning" refers to training or learning in which a subject's behavior is modified by its consequences. The response is initially spontaneous (e.g., touching a blank response grid after receiving a control sample, without prior instruction), but subsequent consequences (e.g., rewards or punishments (e.g., lack of reward)) reinforce or inhibit recurrence of that behavior, thereby teaching the subject how to properly respond. Responses to stimuli, based on operant conditioning, are objective responses, not biased by subjectivity of the respondent.

As used herein, the term "taste" refers to gustatory perception or sensation produced when a substance in the mouth reacts chemically with receptors of taste buds.

As used herein, the term "basic tastes" refer to the five tastes that human taste buds are able to differentiate among. The five basic tastes are typically referred to as sweetness, sourness, saltiness, bitterness, and umami.

A used herein, the term "flavor" refers to the sensory impression of a food or other ingestible substance (e.g., beverage, pharmaceutical, supplement, nutraceutical, etc.), and is determined primarily by the chemical senses of taste and smell. Temperature, texture, and irritant may also contribute to overall flavor perception.

As used herein, the term "taste quality" refers to the characteristic of a taste stimulus either being similar or different from a familiar taste. Taste quality is typically measured with respect to one basic taste. Comparisons to more complex tastes (e.g., chocolaty) may also be regarded as a function of taste quality. In more operational terms, taste quality is the result of the process of discrimination from or generalization to a control taste stimulus (e.g., similarity or difference from sucrose).

As used herein, the term "palatability" refers to the property of taste that determines how likable a substance is in the oral cavity (e.g., how good, or bad, does something taste). Palatability is a sensory characteristic closely associated with the nutritive value of food. For example, highly palatable foods and beverages often are calorie-dense, and as a result tend to be over-consumed. However, some non-caloric sweeteners used in diet drinks are considered to be highly palatable as well. Palatability can be operationally defined as the probability that a food or beverage will be consumed.

As used herein, the terms "testing" or "assessment", refer to any type of venue, device, or methodology for evaluating preferences (e.g., taste, smell, etc.) and/or other characteristics of an individual/subject, multiple individuals, or groups of individuals.

As used herein, a "consequence" is any event, stimulus or appearance (e.g., of a commodity) that is caused by or is temporally related to an antecedent behavior. A consequence that tends to increase the frequency of a behavior that precedes or is causal to that consequence is referred to as a "reinforcer" of that behavior.

As used herein, a "positive reinforcer" refers to a stimulus or commodity that increases the frequency of the behavior that produces it. Examples of positive reinforcers include, but are not limited to, food, money, sex, drugs of abuse, etc. Positive reinforcers may be referred to as "appetitive," for example, in the case of food reinforcers (e.g., the sweet taste of sucrose solution).

As used herein, a "negative reinforcer" refers to a stimulus that increases the frequency of the behavior that removes it from the organism's environment. Examples of negative reinforcers include, but are not limited to, painful stimuli such as shock, extreme cold or heat, the bitter taste of quinine. Negative reinforcers may be referred to as "aversive" or "noxious."

As described herein, appetitive and aversive taste stimuli (e.g., solutions of taste stimuli) can be defined by their rates and/or quantities of consumption (e.g., by a test subject).

A consequence that tends to decrease the frequency of a behavior that precedes or is causal to that consequence is referred to as a "punisher" of that behavior and may include, but are not limited to, stimuli that also serve as negative reinforcers. An event, stimulus, or commodity can be categorized as a reinforcer (positive or negative) or punisher operationally by behavioral impact.

The physical properties of an event, stimulus, or commodity that are detectable by an organism are referred to as "stimulus properties," that can be expressed as a standard that represents the stimulus properties. For example, the concept or standard of "bitterness" can be defined by the representative stimulus of the taste of quinine, and the concept or standard of "sweetness" can be defined by the taste of sucrose. The significance of the stimulus properties to an organism (e.g., a human taste test subject or other subject) is referred to as "salience," and can be a function of stimulus magnitude or the context in which the stimulus occurs.

As used herein, the terms "computer" and "computing device" refer broadly to any type of digital computing or processing device(s) including, without limitation, microcomputers, minicomputers, laptops, hand-held computers, smartphones, tablets, personal digital assistants (PDAs), cellular or satellite-based telephones and any other device or collection of devices capable of running a computer program thereon.

As used herein, the terms "computer program" and "application" refer to any algorithm or sequence of machine-related instructions (regardless of whether rendered or embodied in source or object code) adapted to perform one or more particular tasks. Such computer programs or applications can include any number of differing architectures including, for example, stand-alone applications, distributed applications and object request broker architectures, or other networked applications, and may be stored in any device or any other structured or unstructured digital format including, without limitation, embedded storage, random access memory, hard disk, read-only memory, static memory, optical disc, compact discs (CDs), digital video discs (DVDs), smart card, or magnetic bubble memory.

As used herein, the terms "Internet" and "internet" are used interchangeably to refer to inter-networks including, without limitation, the Internet.

As used herein, the term "memory" includes any type of integrated circuit or other storage device adapted for storing digital data including, without limitation, ROM. PROM, EEPROM, DRAM, SDRAM, DDR/2 SDRAM, EDO/FPMS, RLDRAM, SRAM, "flash" memory (e.g., NAND/NOR), and PSRAM.

As used herein, the terms "network" refer generally to any type of telecommunications or data network including, without limitation, hybrid fiber coax (HFC) networks, satellite networks, telco networks, and data networks (including MANs, WANs, LANs, WLANs, internets, and intranets). Such networks or portions thereof may utilize any one or more different topologies (e.g., ring, bus, star, loop, etc.), transmission media (e.g., wired/RF cable, RF wireless, millimeter wave, optical, etc.) and/or communications or networking protocols (e.g., SONET, DOCSIS, IEEE Std.

802.3, ATM, X.25, Frame Relay, 3GPP, 3GPP2, WAP, SIP, UDP, FTP, RTP/RTCP, H.323, etc.).

As used herein, the term "network interface" refers to any signal, data, or software interface with a component, network or process including, without limitation, those of the Firewire (e.g., FW400, FW800, etc.), USB (e.g., USB2), Ethernet (e.g., 10/100, 10/100/1000 (Gigabit Ethernet), 10-Gig-E, etc.), MoCA, Serial ATA (e.g., SATA, e-SATA, SATAII), Ultra-ATA/DMA, Coaxsys (e.g., TVnet.™), radio frequency tuner (e.g., in-band or OOB, cable modem, etc.), Wi-Fi (802.11a,b,g,n), WiMAX (802.16), PAN (802.15), or IrDA families.

As used herein, the term "processor" refers to all types of digital processing devices including, without limitation, digital signal processors (DSPs), reduced instruction set computers (RISC), general-purpose (CISC) processors, microprocessors, gate arrays (e.g., FPGAs), PLDs, reconfigurable computer fabrics (RCFs), array processors, secure microprocessors, and application-specific integrated circuits (ASICs). Such digital processors may be contained on a single unitary IC die, or distributed across multiple components.

As used herein, the term "server" refers to any computerized component, system or entity regardless of form which is adapted to provide data, files, applications, content, or other services to one or more other devices or entities on a computer network.

As used herein, the term "storage device" refers to without limitation computer hard drives, DVR device, memory, RAID devices or arrays, optical media (e.g., CD-ROMs, Laserdiscs, Blu-Ray, etc.), or any other devices or digital media capable of storing content or other information (e.g., "cloud" storage).

DETAILED DESCRIPTION

The present invention provides systems and methods for testing and assessing preference (e.g., taste preference). In one aspect, various aspects of an individual's taste preferences (e.g., degree an individual likes/dislikes a taste ingredient, degree an individual is willing to pay to keep/exclude a taste ingredient) are tested and assessed. In a further aspect, the taste preferences of a plurality of individuals are tested, assessed, and compared and, optionally, individuals are rewarded for their taste preference(s). Apparatus, computer-readable media and systems for implementing the taste preference assessment and provision of rewards are also provided.

The present disclosure advantageously provides for a taste preference assessment methodology in order to analyze and calculate an individual's, or a group of individuals', taste preference(s) as well as provides the identification of a taste profile for a taste sample(s). Moreover, the disclosure in one exemplary aspect includes an analysis algorithm (e.g., game) specifically configured to determine and calculate taste preference for an individual or group of individuals, and/or taste profile of a sample or population of samples, based on, inter alia, selections (e.g., weighted selections) made by an individual(s) during assessment and/or rewards for selection based upon occurrence of the selection among a population of subjects. Additionally, taste preferences and taste profiles may be associated with an individual and/or taste sample and stored in an individual's user or a taste sample profile and tracked and updated over time for formative and/or summative assessments. Apparatus and systems associated with the taste preference methodologies described herein are also disclosed.

Systems and methods provided herein allow the identification and quantification of various consequences that tend to decrease or increase the frequency of a behavior that precedes or is causal to that consequence as either, respectively, a punisher or a reinforcer (e.g., positive or negative). The physical properties of an event, stimulus, or commodity that are detectable by an organism are referred to as "stimulus properties," that can be expressed as a standard that represents the stimulus properties. For example, the concept or standard of "bitterness" can be defined by the representative stimulus of the taste of quinine, and the concept or standard of "sweetness" can be defined by the taste of "sucrose." The significance of the stimulus properties to an organism (e.g., a human taste test subject or other subject) is referred to as "salience," and can be a function of stimulus magnitude or the context in which the stimulus occurs.

Reinforcers (and punishers) differ with respect to the magnitude of their impact on behavior. This property is referred to as reinforcing "strength" or "efficacy" and is a relative property operationally defined by the behaviors to which the reinforcer (or punisher) is causally related. Reinforcing efficacy is quantifiable by measuring the frequency or magnitude of the behavior that produces the reinforcer. Examples of the frequency (e.g., of a discreet behavioral unit) or magnitude of the behavior that produces the reinforcer that can be measured include, but are not limited to, the number of times a behavior has occurred in order to produce the consequence (or procure the commodity), duration of time engaged in a specified behavior to produce the consequence (or procure the commodity), quantities of a commodity that are consumed, the amount of a limited resource allocated to produce the consequence (or procure the commodity), amount of work, amount of time (e.g., particularly relative to the amount of time engaged in or on other behaviors or activities), and money. For example, rats and humans will drink more water when it is flavored with a sweetener, and will drink less when it is flavored with a bitter substance like quinine, chocolate is consumed more than broccoli, heroin is more addictive than marijuana, etc.

Allocation of resources is a cost a subject incurs to effect changes in the occurrence of an event, stimulus or commodity in the subject's environment, and may be tested, measured, recorded, and/or analyzed using the systems and methods described herein. For example, the amount of time and energy spent, risks taken, the amount of time, energy, and money spent, as well as physical, societal and social risks taken, and the cost a subject will incur to accomplish these activities can be tested, measured (e.g., quantified), recorded, and/or analyzed.

For example, a rat can be trained to press a lever to operate a food pellet dispenser under a Progressive Ratio Schedule of Reinforcement. The number of times the rat must press the lever in order to procure the food pellet is incremented for each serial operation of the pellet dispenser. The number of times a rat will press the lever for the food pellet will reach a limit or "break point." The break point operationally defines the cost the rat will incur or "pay" to procure the food pellet reinforcer. Thus the break point is the value the rat places on the food pellet under those experimental conditions. The number of food pellets a rat "earns" can be plotted as a function of the number of the lever presses required to produce the food pellet to create a demand curve. In further embodiments, the number of food pellets a rat procures (and therefore consumes) is inversely proportional to the number of lever presses required (resource allocated) to produce a food pellet. That is, the characteristics of the function translate to the value of the commodity (food pellet) to the rat. Thus, value (cost paid) predicts the amount of the food that will be consumed if given free access (no cost). With regard to human subjects, in some embodiments of the invention, work is translated into monetary currency with the amount of money spent on a commodity reflecting the amount of the commodity that would be consumed if given free access (no cost) to the commodity. For example, chocolate truffles will be consumed more and therefore a higher price per unit will be paid to procure them. Manipulating the cost per unit of truffles also will result in a demand curve where the amount consumed is a function of the cost.

The term "preference" often is used to describe a test for the reinforcing efficacy (or propensity toward consumption) of a consumable substance. Preference, however, always is some form of relative choice, and is not necessarily predictive of consumption. For example, in a two-alternative forced choice in which subjects are instructed to choose their preference between a 1 mM quinine solution and 0.1 mM solution of quinine, the latter is likely to be preferred. However, the 0.1 mM solution is not likely to be highly consumed. Even with a larger set containing multiple samples from which to select a preference, or to which a subject can rank-order the multiple samples according to a hierarchy of preferences, the result is not necessarily directly predictive of consumption. A preferred sample could be predicted to be consumed more than the less preferred samples, but no determination or estimation can be made on the absolute magnitude of the sample's consumption. This is especially true in terms of a demand curve function.

Scaling methods, in which subjects are instructed to use a numeric scale to indicate the magnitude of their preference do not circumvent the problem—they still are relative. Thus, preference tests unsuccessfully conflate relative choice with the desired outcome of predicting consumption.

In contrast, and as described in detail herein, the invention provides systems and methods for determining and/or quantifying likelihood of consumption (e.g., predicting consumption. In some embodiments, a measure (e.g., quantification) of reinforcing efficacy is used for predicting consumption.
Exemplary Taste Preference Assessment System and Methods In one non-limiting embodiment, a method is provided that includes providing one or a plurality of subjects and a taste preference system, where the taste preference system comprises an initial sum of goods to be used (e.g., spent, traded or the like) by the subject (e.g., a pot of money, number of goods, or other set of items that provide value to the subject); a plurality of taste samples (e.g., one or a plurality of ingredients) to be tasted/tested by the subject; means for the subject to record the subject's decision to accept/retain or reject/exclude a taste sample from the plurality of taste samples; means for the subject to identify and record a value of a portion of the sum of goods with the decision to accept/retain or reject/exclude the taste sample from the plurality of samples; means for comparing taste samples retained or excluded by a subject with either a control or with other subjects; and means for compensating a subject (e.g., based upon samples retained or excluded).

For example, in one embodiment, the invention provides a taste preference system containing taste samples, where the system randomly selects the samples from a plate of samples (e.g., via an automated component (e.g., an automated robotic arm and/or pipette)), makes the samples individually available to a subject for testing, prompts a subject (e.g., via computer screen/monitor) to make a choice to retain or exclude (e.g., based upon like or dislike, respectively) a sample, upon making a choice, provides the subject the ability to weigh the value of making the choice to retain or exclude (e.g., via providing a cost of execution presentation (e.g., via computer screen/monitor) that a subject adjusts to scale associating the cost of executing the choice with the probability of outcome for the choice), and, once entered into the system (e.g., via a subject entering the value of the cost execution), records the subject's choice, the value for the choice (e.g., the subject's initial sum of money is reduced accordingly) and identifies the sample retained or excluded (e.g., in a memory component of the system).

In still another aspect, systems and methods described herein are used in or as a game (e.g., for one or a plurality of subjects) to identify a taste profile (e.g., of one or a plurality of samples). In one embodiment, taste preferences of one or more subjects are used to generate a taste profile for a taste sample or plurality of taste samples (e.g., how much a particular sample is liked/disliked). For example, in one embodiment, for each round or trial of a game a subject is tasked with generating a plate of taste samples from a plurality of taste samples that the subject identifies as good/pleasant tasting, and starting with an initial sum of goods (e.g., a pot of money), the subject tastes a sample (e.g., from a population of taste samples being tested) and the subject makes a determination of whether to keep or not keep a taste sample based upon whether the subject likes or dislikes the taste of the sample. For example, if a subject likes a sample the subject chooses to include the sample (e.g., for generating a plate of retained/kept samples) and if the subject does not like a sample the subject chooses to exclude the sample (e.g., from a plate of retained, liked samples). Choosing to include or exclude a taste sample may be designated using any means. In one embodiment, pressing a touch screen configured with the options to "include" or "exclude" are used by a subject to designate whether the subject wishes to include or exclude a taste sample, and in order to execute the include/exclude command, the subject selects a monetary value associated with a probability of guaranteeing the outcome of the command with the monetary value subtracted from the initial sum of good (e.g., pot of money) when the decision is executed (e.g., using a sliding scale that monetizes based on probability the likelihood of keeping/excluding). In one embodiment, a subject is compensated at the end of a round by how many samples in the subject's plate are common to the cumulative set of samples that are present in the plates of all subjects (e.g., that are participating in the round, or that generated a plate using the same population of taste samples being tested).

Instructions are provided, in one embodiment, to a subject/game participant on the overall structure of the game. For example, subjects are told that they are going to create a plate of the best tasting ingredients that will be evaluated by a consumer market for approval. Furthermore, the subject is instructed that the plate will be created by evaluating samples one-by-one and adding them to or excluding them from the plate (that is, the plate of retained/included samples). The subject may further be instructed that there is a cost to making the plate. For example, in one embodiment, at the start of the game, each subject is given a "pot" of money, an initial amount of capital, from which to draw to pay for the creation of the plate (e.g., as described herein, the subject will associate a weight/value from the sum of money that will increase the probability that a sample is added or excluded from the plate). Upon completion of a round(s) of sampling and generation of a plate of retained samples, the plate is entered into a market for an approval (e.g., by a population of subjects). In some embodiments, the market rewards the subject according to the quality of the plate. The composition of the market may or may not be shared with the subject (e.g., the market might be virtually created by any of a number of algorithms, the market may comprise other players who are simultaneously creating their own plates, or the market may be derived from an existing, growing database (to which the subject will be adding the results of his or her session)).

Figure 2:
FIG. 2 shows a non-limiting example of a sliding scale of probability for inclusion/exclusion, where a subject uses a computer mouse or buttons to move the bar to place probability of inclusion/exclusion of a taste sample within the subject's plate. Bar indicates the probability to nearest $100^{th}$. Capital is adjusted as bar moves. Upon the subject determining the amount the subject is willing to pay to include or exclude the sample, the subject effectuates the decision by pressing or clicking execute.

The invention is not limited by the mode of operation of the game. Indeed, variations of the game may be made in order to generate taste sample preferences and/or data. In one non-limiting example of a basic step-by-step progression of game operations, the game starts with an automated random selection of sample from a plate of taste samples (e.g., a 96 well plate of taste samples, containing 96, 48, 24, 12 or fewer different and distinct taste samples (e.g., individually, in duplicate, in triplicate, etc.) When a sample has been retrieved (e.g., using an automated pipette), the subject is prompted by the system to self-administer the sample. The invention is not limited by the type of system used to handle, dispense, and/or record samples and game choices. In one preferred embodiment, a system described in U.S. Pat. No. 9,841,897, hereby incorporated by reference for all purposes, is used. A "Choice Screen" then is shown to the subject, and subject is prompted to make a choice to include or exclude the sample from the plate the subject is creating (See FIG. 1). In one embodiment, a time limit—also known as a "limited hold," is applied to dissuade the subject form taking too long. For example, if the time limit is exceeded, the game can be configured such that the subject loses that specific trial. Upon making the choice, the subject is presented with a new screen entitled "Cost of Execution Screen." The Cost of Execution Screen requires the subject to adjust a scale associating the cost of executing the choice with the probability of outcome for the choice. A non-limiting example of a sliding scale of probability for inclusion/exclusion is show in FIG. 2. Upon the subject determining the amount the subject is willing to pay to include or exclude the sample, the subject is presented with an "Execute" button on the screen, and upon pressing it, the decision is recorded, the sample is included or excluded, and the amount of money spent by the subject is reduced from the subject's initial pot. In one embodiment, the display/monitor depicts the summation of the subject's decisions to include or exclude samples on the subject's plate (See, e.g., FIG. 3). The display updates the plate contents on each trial. Some previously included samples might disappear (on a probabilistic basis) if the price that was paid for inclusion was not high. The process repeats until the sample set is exhausted/all samples are tested at which time an indication of the end of the round in the game appears on the screen. In some embodiments, the monitor/screen the switches to "Market Evaluation," which displays additional visual stimuli indicating progress of market analysis thereby keeping the subject engaged until a market reward is determined. The invention is not limited by the type of data displayed. In some embodiments, a timer is shown on the display. In other embodiments, virtual market activity representing real-time bidding (whether based on actual events or virtually fabricated by the computer) are shown on the display. Ticker-prices like a stock market readout or a slot machine may be shown on the display. Virtual bidders and bidding activity (e.g., in an auction for plates (one of which will be identified as the subject's) may also be shown on the display. In some embodiments, when "Market Evaluation" is complete, the subject is provided with a new screen that displays the price offered to the subject by the market for the subject's plate of retained samples. In some embodiments, the subject is paid the remainder of the original pot and the Market Value reward.

The invention is not limited by the means or method of rewarding a subject (e.g., providing an incentive) for creating a plate (e.g., in a game described or provided herein). Indeed, a subject may be rewarded in a variety of different ways. In some embodiments, a direct payment is made to a subject that compensates the subject (e.g., for loss due to expenditures) or that results in a net profit to the subject (e.g., an amount that exceeds the sum of expenditures.) In some embodiments, a value that equates to monetary compensation, assigned by a panel of judges is used. In other embodiments, a value obtained from an auction where participants submit bids that reflect their individual assessments on the worth of each or all components of the subject's created plate is used. In still other embodiments, a reward based on the number of components of a created plate that also are replicated in at least one other subject's created plate is used. In some embodiments, a reward that is based on consistency of a subject's value assessment with information obtained from a database of values assessed for commodities is used. The invention is not limited by the type of database. In some embodiments, the database is one that is progressively populated by results from repeated tests of each of the commodities (e.g., taste stimuli, samples, etc.). In other embodiments, the database is obtained from external information (e.g., an external database of relevant information) that exists independent of the systems and methods and data obtained therefrom described herein. Similarly, the invention is not limited to any specific way of rewarding a subject. Indeed, in some embodiments, one or more of the above ways of rewarding a subject are used in combination with one or more other ways of rewarding a subject. In some embodiments, a Virtual Market is used to rewards a subject. As used herein, a "Virtual Market" refers to a computer algorithm that replicates any of the above- and herein-mentioned ways of rewarding (e.g., providing incentive to) a subject (e.g., for creating a plate).

The invention is not limited by how a Virtual Market functions. Indeed, the Virtual Market may replicate any of the ways of rewarding a subject described herein. In other embodiments, the Virtual Market may function by, among other steps, adding a fixed pre-determined or randomly generated sum to the amount spent by a subject in a plate creation step; or multiplying the sum of the subject's expenditure by a fixed or by a randomly generated variable; or a combination of the two. In other embodiments, the Virtual Market may derive a value for monetary reward from a mathematical function that incorporates input from a set of variables (e.g., including, but not limited to, the amount spent by the subject in the plate creation, any additional quantifiable aspect of the subject's current or past performance, or any of the variables mentioned above, or any additional variables). In still further embodiments, the Virtual Market utilizes an artificially intelligent algorithm that is trained by existing information on values associated by any means to examples that are equivalent to or share varying degrees of similarity to the samples tested by the subject (e.g., in the creation of a plate). In some embodiments, the Virtual Market utilizes an artificially intelligent algorithm that is composed of virtually created judges. In other embodiments, the Virtual Market utilizes an algorithm that cycles, randomly or otherwise, through multiple established strategies. In still other embodiments, the Virtual Market utilizes an artificially intelligent algorithm, trained by a cumulative body of information about the performance of subjects across multiple tests, that results in a strategy that could be revealed to the subject without influencing the subject's choices in creating a plate Systems and methods of the invention may be used to assess and determine taste discrimination (taste quality) and preference (palatability), individually or in combination (e.g., in a single assay/round). In some embodiments, a subject(s) that utilizes the systems and methods of the invention (e.g., participates in a game described herein) is trained for taste discrimination by teaching the subject to associate the taste(s) of standards to specific coordinates on a touch screen (e.g., as described in U.S. Pat. No. 9,841,897, hereby incorporated by reference for all purposes). For example, using a computer interface/touch screen monitor, a subject is trained using control stimuli to respond to a set (e.g., range) of stimuli with a corresponding set (e.g., range) of responses. For example, a subject is trained using control stimuli that reflect various values along a range for a particular characteristic; then, when a subject is given a test stimuli, the subject can accurately and objectively place the stimuli along the range for that characteristic (e.g., even if the subject has not been made aware of the identity of the particular characteristic). The subject need not be consciously aware of what characteristics he/she is responding to, but rather has been conditioned to objectively provide responses. After such training, when a taste test sample is provided, the subject's response is an objective assessment of the taste characteristics, based on the training, not biased by subjectivity. The subject's trained response is based on the subject's ability to discern and distinguish the characteristic(s) of the stimuli (a property of the subject's nervous system, not a reflection of the subject's judgment).

Figure 4:
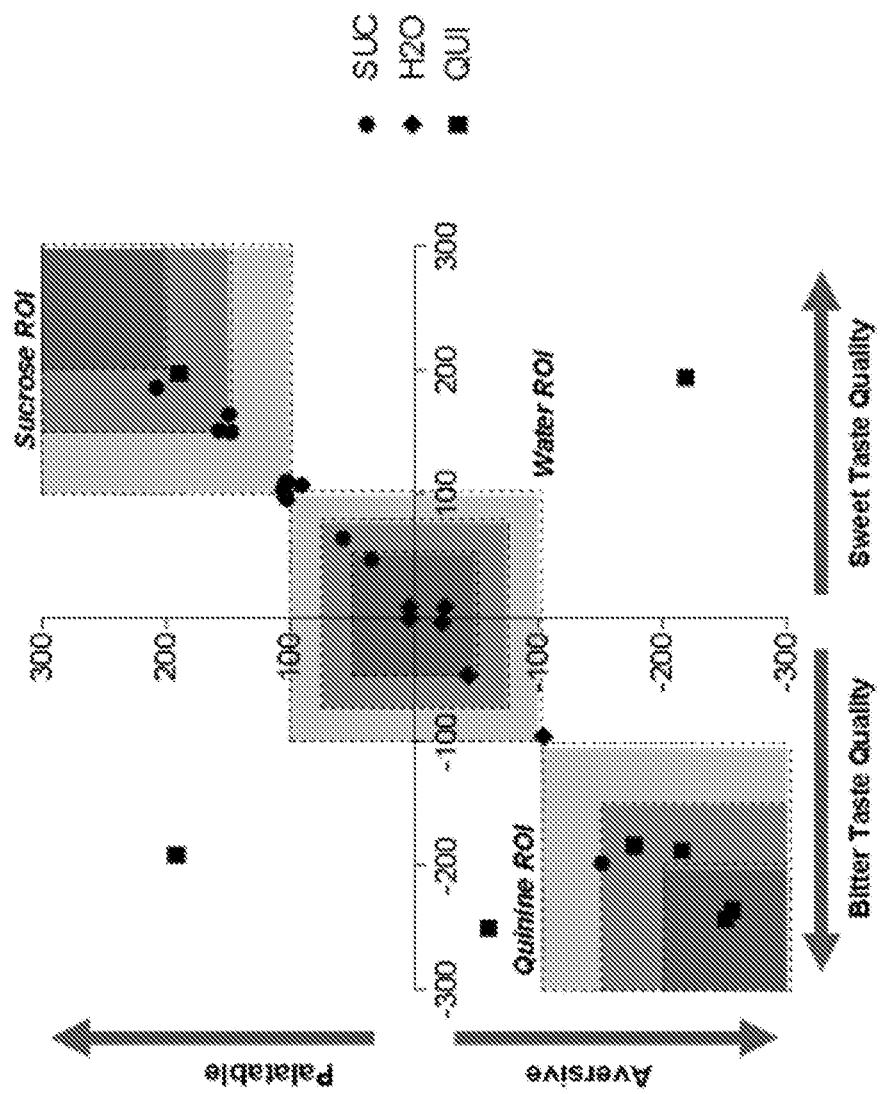
FIG. 4 depicts regions of interest (ROIs) that are programmed to be associated with desired tastes standards for use in training a subject to objectively identify taste standards prior to utilizing systems and methods of the invention.

For example, a subject can be trained via being instructed to find the point-carrying commodities within the field (a Cartesian grid) of a touch-sensitive monitor using taste stimuli as clues to locations. The regions of interest (ROIs) are programmed to be associated with desired tastes standards (e.g., 100 mM sucrose (sweet), water (neutral), or 1 mM quinine (bitter)). Concentric ROIs (different shades of gray) represent ranges of point values for responses made within the ROIs. Responses made outside of the ROIs result in a grayed-out screen. Positive x-axis represents sweet taste quality, negative x-axis represents bitter taste quality. Positive y-axis represents palatable (appetitive) taste, negative y-axis represents aversive taste. Values on axes are pixels. Data points show locations of touch-responses made on the monitor following the subject's sampling of sucrose, water, or quinine. Any desired number of standards can be randomly presented to the subject for training. Accuracy can be determined by measuring the distance from the x,y coordinates of the subject's response to those of the ideal target (see FIG. 4). Distance is calculated using the Pythagorean equation, and each point in the graph represents the value of the distance in pixels on each trial. Additional taste stimuli, 100 mM NaCl (salty) and 10 mM citric acid (sour), can also be utilized as taste standards.

Thus, in some embodiments, once a subject is sufficiently trained for taste discrimination, the subject can enter into/play a preference game using the systems and methods of the invention. In a first step, the subject is required to identify taste quality/discriminate between certain tastes. In order to accomplish this, the subject tastes and then touches a screen (e.g., shown in FIG. 4) at a location he or she has been trained to associate with a standard taste reference. The touch response occasions a consequence, for example, a series of taste standards can be used a controls in this first step (e.g., control trials), with a reward for correct association, or a penalty for incorrect association/discrimination. Once the subject is sufficiently trained for taste discrimination, the subject can enter into/play a preference game using the systems and methods of the invention. Accordingly, in some embodiments, once trained, a subject can proceed to a second step, where the subject is presented a plurality of taste samples, one at a time, and the subject has to decide whether to include or exclude the taste sample from a plate the subject generates. After deciding whether to include or exclude the taste sample, the subject then decides, in a third step, the value of keeping or excluding the taste sample (e.g., as shown using a sliding scale of probability depicted in FIG. 3). Thus, in some embodiments, the resulting data set categorizes samples according to their taste quality and palatability. The invention is not limited by the type of taste characteristic of the taste samples that the data set categorizes. Samples can be characterized by association with different categories of basic tastes including, but not limited to, salty, sweet, bitter, sour, umami, neutral (no taste), or more complex categories of taste such as chocolatey, spicy, medicine-like, etc.). As described herein, the taste samples tested and included or excluded by a subject are also associated with a value of preference by the means of steps 2 and 3 described above. In some embodiments, the preference value of step 3 provides information that is independent of taste quality. In other embodiments, the preference value is associated with taste value through a probability distribution.

The invention is not limited to determining taste preference alone. In some embodiments, the systems and methods of the invention are used to assess and characterize the effects of other sensory (non-taste) influences on preference (e.g., taste preference). For example, within a game environment of the invention, a monitor/display can present visual stimuli on the touch screen (e.g., during the time period that a subject is making a decision of whether to include/exclude a sample and/or when deciding how much value will be spent to include/exclude a sample. Examples of visual stimuli include, but are not limited to, change of color of the screen, presentation of shapes of any kind, presentation of scenery (e.g., environments, locations, etc.), presentation of images (e.g., of people, animals, objects, cartoon characters or shapes), presentation of words, presentation of marketing information (e.g., brand names or other brand information (e.g., logos)), presentation of auditory stimulation (e.g., music), presentation of sounds (e.g., pleasant sounds such as a gentle bell tone, noxious sounds such as a loud buzzer, etc., a recording of spoken words (e.g., male or female voices), nature sounds (e.g., bird calls, weather, waves, etc.). In some embodiments, one or more odors are presented to a subject during taste preference assessment.

Figure 3:
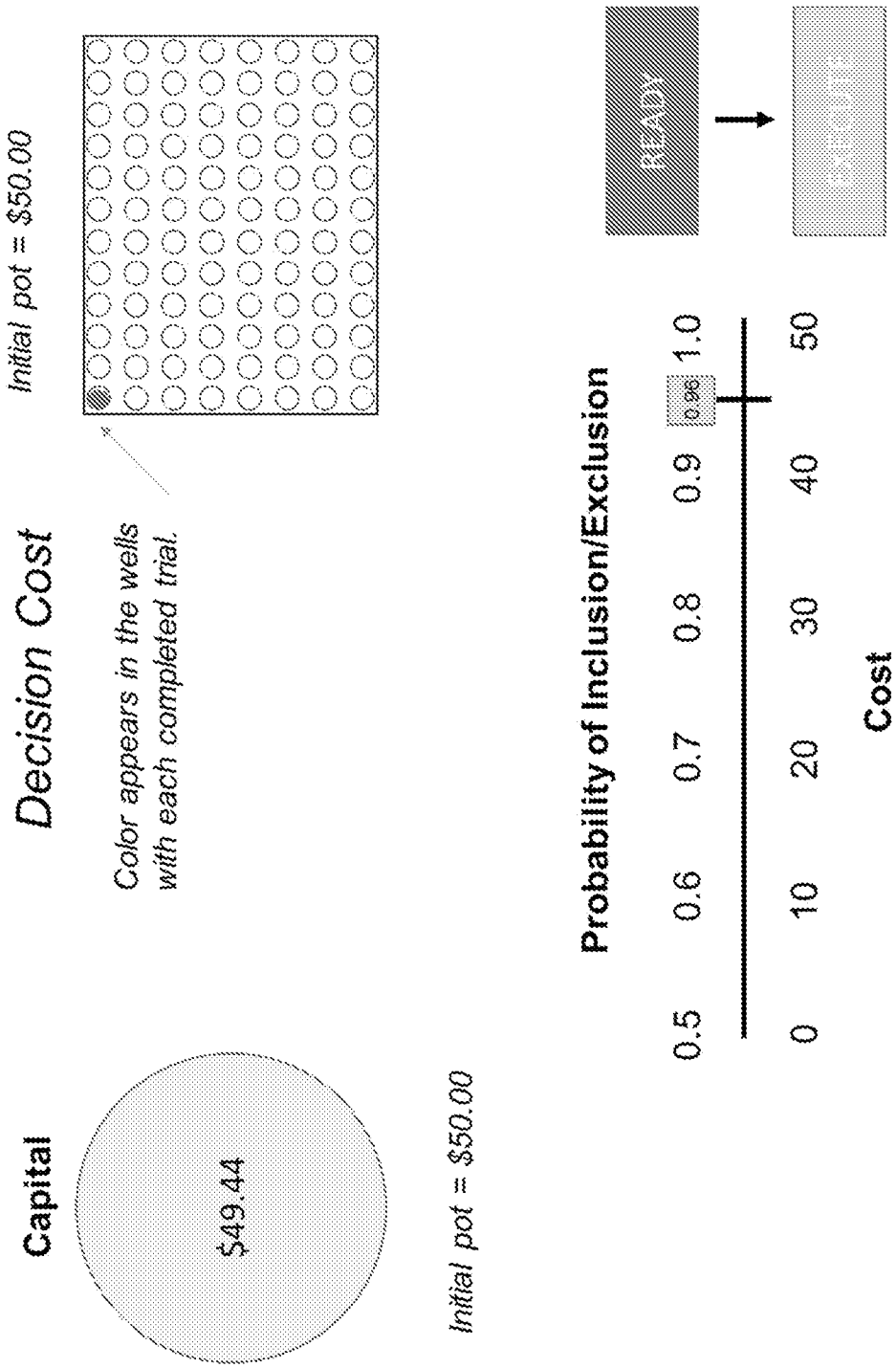
FIG. 3 shows a non-limiting example of a display shown to a subject, wherein the subject is presented with an "Execute" button, and upon pressing it, a subject's decision to include or exclude a taste sample is recorded, the sample is included or excluded, and the amount of money spent by the subject is reduced from the subject's initial pot. The display updates the plate contents on each trial.

The invention is not limited by the means of quantifying the inclusion/exclusion decision. In some embodiments, a sliding probability/expenditure scale is used (e.g., as shown in FIG. 3). Any cost/probability scale may be used as long as the cost/probability scale determines the probability that the choice made—to include or to exclude—will be associated with and carried out for the final plate composition. In some embodiments, the probability of inclusion/exclusion will range from 0.5 (random) to as high as 1.0 (certainty). In other embodiments, the probability scale has values to a decimal to 1-2 significant figures (for example, if needed, the range can be different to achieve specific behavioral outputs, and therefore will be an input variable when programming the test). In some embodiments, probability and value are used to relate the point value to familiar monetary units (e.g., a probability of 1.00=cost of $1.00, probability of 0.5=$0.50, etc.). In some embodiments, the subject pays for a particular probability that their choice will be carried through to the end of the session (completion of the subject's plate). The invention provides that ability to have a range of monetary values associated with each probability. For example, since the subject can be remunerated in real money by a game scenario of the invention, the range can be defined in any way that accommodates an investigator's/researcher's budget (this is an input variable when programming the test (e.g., $0.00 to $1.00, $0.00 to $10.00, $0.50 to $1.00, $0.50 to $10.00, etc.)). In some embodiments, the range is set by cost-effectiveness in engaging the subject and ensuring reliable performance). In some embodiments, the size of the initial value of goods (e.g., initial pot of money) is based on resources and/or empirical determination of the effects the initial and final pot magnitude will have on a subject's behavior. In some embodiments, a cost/probability scale is determined empirically to achieve a desired end (e.g., optimal subject behavior, optimal taste preference identification, etc.).

The invention is not limited by the way a subject is prompted to associate a cost that the subject is willing to pay to include/exclude a taste sample. Indeed, after making a choice to include/exclude on the "Choice Screen," a subject can be prompted by the computer/monitor on the "Cost Screen" to move the cost/probability scale to the desired location, the prompt being any of a number of cues (e.g., visual cues appearing on the screen, such as a rectangle with wording such as "Prove you are Willing to Pay" "Cost to Execute" "Set Probability of Inclusion or Exclusion" or other prompt.

The invention is not limited by the appearance or configuration of the cost/probability scale. In some embodiments, a cost/probability scale is a linear scale labeled with "Cost" in increments of monetary units on one side and "Probability" from 0.0 to 1.0 (or any range there between (e.g., 0.5 to 1.0)) on the other side. In other embodiments, probability is expressed in percentage units as in "75% chance of inclusion." In some embodiments, the scale is presented as a circle, pie chart, bar graph, frequency distribution, or other pictograph, showing cost on one dimension and probability on another. As described herein, when a subjected is prompted (e.g., after making a decision to include or exclude a taste sample), the subject adjusts the scale, and in some embodiments, simultaneously receives visual feedback from the scale. In further embodiments, the subject may also receive visual cues elsewhere on the screen (such as a representation of the pot diminishing according to the subject's actions). A subject can adjust, and watch the impact of adjustments (e.g., how increasing the probability of inclusion alters the amount of value required), freely until they are satisfied with the location of the decision on the cost-probability function. Once the subject is satisfied with cost-probability point, the subject will press a visual indicator on the screen for execution of the decision and the associated cost. The invention is not limited by the means of executing the decision. The action can be achieved by pressing the touch screen with a finger or stylus, or by selecting with a mouse. The visual indicator could be a green rectangle with wording such as "Execute." In a further embodiment, there is a virtual representation of the subject's plate, appearing on the "Cost Screen," or on all screens so that the subject's plate presence is constant. In some embodiments, the plate initially appears as an empty microtiter plate (e.g., an empty 96-well plate or a 24-well plate). After the completion of each trial (e.g., after each taste sample is tested and a decision to include or exclude is executed), the virtual representation of the subject's plate can be updated, so that the wells fill (e.g., with an indicator color) as the subject progresses through the session/game. Thus, the subject receives visual feedback of progress through the taste samples. The visual feedback also provides, in some embodiments, a track record of the subject's actions as the session progresses. For example, the impact of the probability on inclusion or exclusion (for example, whether samples disappear that had been included at a lower cost, or appear that had been excluded at a lower cost) can be shown. In some embodiments, the visual feedback is programmed to occur continuously as a function of time during the session. In other embodiments, the visual feedback is programmed to occur discretely on each trial. In some embodiments, the executed decision to include or exclude appears in the virtual plate according to a color code scheme.

In some embodiments, a subject/game participant includes tastes samples in a plate, and excludes other taste samples, thereby creating a final plate of subject's retained/included taste samples. Upon completion of the subject's final plate, in some embodiments, the plate is evaluated by a consumer market. In some embodiments, the Consumer Market is formed by a cohort of other subjects/participants that also evaluated the same set of ingredients (e.g., at the same time as the subject, or at a different time) and that created their own final plate. At the end of all sessions in a cohort, a "Grand Collective Plate" is generated (e.g., using software to analyze the identification of taste samples present in each subjects'/participants' final plate) via identification of the taste samples that occur in each of the subjects'/participants' final plate. Thus, in some embodiments, the "Grand Collective Plate" contains taste samples that were chosen to be included with high probability (i.e., that subjects paid a premium to include) by a plurality (e.g., a majority) of the subjects/participants (e.g., high replicates appearing in a plurality of the subjects' plates). In some embodiments, the "Grand Collective Plate" contains taste samples that were chosen to be included with a decreased probability (e.g., not a high probability because the subjects were not willing to pay a high price to retain/include the sample). In still other embodiments, the "Grand Collective Plate" contains taste samples that were chosen to be excluded with high probability (e.g., as evidenced by the absence of replicates among the plurality of subjects/participants).

For example, FIG. 5 depicts a composite plate (e.g., Grand Collective Plate) derived from four taste test subjects' responses to 8 taste samples/ingredients, each sample presented 12 times in a single round. Each of the subject's preferences to the 8 samples/ingredients are translated into a composite (e.g., Grand Collective) plate. In this non-limiting example, the sliding Cost/Probability scale ranges from 0.5 to 1.0, so that, for example, if a subject spent none of his/her initial pot (e.g., of money) on creating a plate, then all of the 8 samples will appear in their final plate, on average, with 6.5 replicates. Thus, any ingredient that appears in a subject's final plate more than 6 times is considered appetitive (or "liked") to that subject because they paid something to keep them in, and 6 or fewer times is considered aversive (or "disliked") because they paid something to keep them out. FIG. 5 shows how, in this example, the data translate from each individual's preferences to a more generalized dataset. The individual preferences can be stored (e.g., in a database and/or memory component of a system described herein), and as the number of preferences recorded (e.g., from the same or different subjects) grows (e.g., as the database grows), individual subjects can be grouped according to their preferences which, in some embodiments, leads to the identification of subpopulations of subjects reflecting localized preferences. In further embodiments, the identification of subpopulations of subjects reflecting localized preferences provides data and/or information serving as a basis for product differentiation. In still further embodiments, data gathered and stored regarding composite plates (e.g., "Grand Collective Plates") is used to draw generalizations regarding the population at large (e.g., to identify taste samples/ingredients that are appetitive or that are aversive (e.g., that can be included or that should be excluded, respectively, from a commercial product)).

The invention is not limited by the means of rewarding subjects/participants. As described herein, the overall cost of a subject's final plate is determined by the price the subject pays (drawn from their "initial pot") to include or exclude each ingredient/sample as it is sampled one-by-one. In some embodiments, once a subject's final plate is assembled, and the better his/her plate is judged by the consumer market, the greater the subject's reward. Accordingly, in some embodiments, a subject manages his/her pot according to his/her expectations that what they value in the creation of their final plate will also be valued by the Consumer Market. Thus, in some embodiments, a subject's expectation of return by the Consumer Market is determined on a trial-by-trial basis (e.g., in a first round of testing). In further embodiments, the expectation of the subject for market reward is directly reflected by the price paid by the subject on that trial. In still further embodiments, by the end of a session, a subject will have ended up spending a majority of the pot for a set of samples the majority of which the subject found highly preferable, and therefore expects that the Consumer Market also will find preferable and will in turn reward the subject accordingly. In like manner, the subject will spend less on a set of samples that, overall, the subject finds less appealing, and therefore will retain more of the pot. The expectation will be that the Consumer Market also will not find the overall set to be appealing, and will be less likely to return a larger reward. In some embodiments, subjects that "hedge their bets" will be penalized in that they could have earned much more from the Consumer Market if they had committed more of their pot to guarantee the inclusion of highly palatable samples or exclusion of unpalatable ones (probability of inclusion or exclusion is set by the price the subject paid on that trial.) Thus, in some embodiments, a subject is remunerated the amount remaining in the pot, and the amount of Consumer Market reward. Consumer Market reward can be determined using any one of several possible algorithms. For example, a non-functional Market algorithm may be used in which case a fixed amount is added to the subject's pot at the end. In the case of a non-functional market, the consumer market does not actually exist in a functional way. In some embodiments, the subject is not informed of the non-existence of the consumer market. A Functional Market Remuneration algorithm may be used. In a Functional Market Remuneration algorithm, each subject in the cohort (the Consumer Market) will be remunerated based on the number of samples in the subject's individual plate that are replicated in the "Grand Collective Plate." In some embodiments, each sample in the subject's plate would be multiplied by the number of replicates of a given sample occurring in the "Grand Collective Plate." For example, Sample 1 was presented to Subject A ten times in the plate creation phase (first round) and ended up as 8 replicates (based on the price paid by subject A) in Subject A's final plate. Three other subjects, comprising the Market, also ended up with many replicates of Sample 1 in their final plates, resulting in a "Grand Collective Plate" containing 28 replicates of sample 1. If the value for a replicate is $0.10, then Subject A would be rewarded with a sum of 28×$0.10=$2.80 for Sample 1. The process would be repeated for each additional sample (e.g., sample 2, sample 3, etc.) that is replicated in the "Grand Collective Plate." In some embodiments, the subject is penalized for any of the samples remaining in his/her individual plate that was not replicated (or that was not replicated enough by a predetermined criterion) in the "Grand Collective Plate." Thus, in some embodiments, the penalty results in a reduction of the Consumer Market remuneration. In some embodiments, a Subject is remunerated according to the percentage match between the composition of the subject's individual plate to that of the "Grand Collective Plate."

The invention is not limited by the number of individuals per cohort. Indeed, cohorts can be designed according to any experimental or commercial objectives. In some embodiments, the number of individuals comprising a cohort is determined by the level of uncertainty the investigators are willing to tolerate with respect to generalizability and statistical power. The number of individuals in a cohort may be 2, 3, 4, 5, 6, 7, 8, 9, 10, 11, 12, 13, 14, 15, 16, 17, 18, 19, 20 or more (e.g., 25, 30, 35, 40, 45, 50, 55, or more, or a number there between). For example, in order to generalize to the largest consumer markets, the number of subjects in a cohort might be 50 or more. In some embodiments the subjects are reflective of the demographics of the population at large. In other embodiments, the subjects do not reflect the demographics of the population at large, but rather only a specific group (e.g., of a specific age, sex, nationality, etc.). In some embodiments, subjects within a focus group, concentrating on a sub-population that might have specialized taste preferences, are used to comprise a cohort (e.g., adult women aged 21-45, adult males aged 50-65, children aged 5-12, males and females of all ages identifying as "Asian," people from a specific country or state, etc.). In some embodiments, because these specialized groups are less diverse, and therefore are expected to create less variability in data, they require fewer subjects for forming cohorts. In some embodiments, for a relatively homogeneous population, a cohort size of 2-10, 3-9, 4-8, 4-7, 4-6, or 4-5 individuals can be expected to achieve generalizable statistical power.

The invention is not limited by the type of data generated, assessed and/or characterized using the systems and methods described. In some embodiments, fundamental data includes the price paid by each individual subject for each sample as a reflection of the subject's value of the sample. In some embodiments, the probability that resulted for inclusion/exclusion of each sample is a reflection of the perceived importance to the subject of his/her actions. In some embodiments, the overall composition of the "Grand Collective Plate" is an indication of the generalizability of the results. In some embodiments, the data generated, assessed and/or characterized by systems and methods of the invention identify appetitive tastes. For example, in some embodiments, systems and methods provided identify, among any random set of ingredients, the best tasting ingredients. In some embodiments, systems and methods provided identify, among a focused set of ingredients, the best tasting ingredients. The invention is not limited by the type of focused set of ingredients. In some embodiments, the focused set is a salty class of ingredients, a sweet class of ingredients, a savory class of ingredients, or any other class of ingredients. In some embodiments, systems and methods provided identify, the best tasting ingredients among salt substitutes (e.g., potassium chloride), individually or in a product. In some embodiments, systems and methods provided identify the best tasting ingredients among non-nutritive sweeteners or other ingredients that have bitter off tastes or that are not preferred tastes because of the temporal aspects of the sweet taste sensation (e.g., lingering sweet aftertastes). In some embodiments, systems and methods provided identify the best tasting ingredients among complex taste categories (e.g., savory or umami). In some embodiments, systems and methods provided identify the best tasting ingredients among mixtures (e.g., by exploiting a 96-well plate matrix for rapid combinatorial exploration of different ratios of ingredients). In some embodiments, systems and methods provided identify the best tasting ingredients among a set of ingredients relative to a "gold standard" within a set. In some embodiments, systems and methods provided identify a rank ordering of among ingredients within and across sets. In some embodiments, systems and methods described herein provide for building a database from all tests for ad hoc analysis across datasets of any kind. In some embodiments, systems and methods provided identify ingredients among aversive taste ingredients. For example, in some embodiments, systems and methods provided identify ingredients with varying degrees of probability of being left out of a final plate (e.g., the most aversive will never, or almost never, be included in a final plate, and as aversiveness declines, appearance in final plate(s) will increase). In some embodiments, systems and methods provided identify the best tasting ingredients for use in pharmaceutical formulations. For example, in some embodiments, systems and methods provided identify and associate taste discrimination results (e.g., from a screen of bitter blockers) to acceptability (preference). This is particularly useful in cases where the aversive taste of an active pharmaceutical ingredients (API) is not itself ameliorated (e.g., bitter blocking per se has not been effective) but the taste of the vehicle has been formulated to improve overall acceptance regardless of the full bitterness imparted by the API. In some embodiments, systems and methods provided identify novel ingredients of which the taste properties have not been defined.

Datasets generated utilizing the systems and methods of the invention allow predictive model building (e.g., of taste function) through curve-fitting analyses. For example, nonlinear regression can be used to mathematically and rigorously define the relationship, for example, between concentration of a taste test sample and the taste sensation evoked in a subject (e.g., tested and recorded utilizing the systems and methods described herein). The large, chemosensory datasets made available utilizing the systems and methods disclosed herein may be utilized for trend analyses (e.g., by linear, nonlinear, multivariate, simple, Bayseian, least squares, or polynomial regression) that predict future performance (e.g., of taste-based products) in larger groups or in the commercial marketplace. These capabilities are not available or not achievable with conventional methods (e.g., of taste measurement), which require large numbers of subjects that evaluate only one, two or a few different samples per test. Because of the low throughput of data collection, the heretofore available conventional taste tests are dependent on statistical hypothesis-testing (e.g., ANOVA, Chi-squared tests, t-tests, or any non-parametric tests such as Kruskal-Wallis ANOVA, Mann-Whitney U, Wilcoxon Rank Sum, or Cohen's Kappa tests). In further embodiments, systems and methods of the invention make possible the tracking and recording of the responsiveness (e.g., taste responsiveness) of individual subjects over a period of time (e.g., over hours, days, weeks, months or years).

In certain embodiments, the methods and device of the invention reduce the number of subjects conventionally required for taste sample testing. In some embodiments, the number of subject is the same as conventional testing, but the number of data points is increased. The methods and devices allow the testing to be analyzed in an objective, data-driven manner. For example, devices and methods of the invention make possible few subjects (e.g., 1-10, 2-8, 3-4, etc.) generating many data points (e.g., 100-1000) instead of many subjects (e.g., 20-60) generating relatively few data points (e.g., 40-120). The present invention therefore makes available large sets of data (e.g., large data sets (e.g., with consistency among the sets due to the data being generated from a relatively small set of subjects)) that are amenable to regression analysis (e.g., predictive modeling, Bayesian statistics, etc. for example, by linear, nonlinear, multivariate, simple, Bayseian, least squares, or polynomial regression.)

In some embodiments, training and testing are performed at a testing facility and/or monitored/administered by a test monitor/administrator. In other embodiments, training and testing are performed by the subject, in the absence of monitoring/administration. In some embodiments, a device specifically designed to perform the training/testing is provided to the subject (along with appropriate samples), and the device administers the sample and record the responses appropriately (e.g., administering control samples in a manner to appropriately train the subject, switching from training to testing once the subject has provided sufficiently correct response). In some embodiments, training is administered according to an algorithm that guides the subject toward being test ready. In some embodiments, a subject is able to use his/her personal device (e.g., smart phone, personal computer, tablet, handheld device, etc.) to perform the test/training. In such embodiments, the subject is provided with the samples (e.g., actual physical samples, digital versions, etc.). In some embodiments, a software, program, application, etc. is installed on the subject's device to perform the training/testing. In some embodiments, the device instructs the subject on the order of samples, or provides the samples to the subject in the proper order. In some embodiments, the subject records responses on their own device.

In some embodiments, subject information (e.g., biographical information, age, sex, medications, known food allergies, etc.) is recorded and correlated with the results of the training/testing. In some embodiments, subject information is entered by the subject (e.g., at the UI). In other embodiments, an administrator enters the information. A subject may be issued (e.g., automatically) an ID number or username (e.g., to allow anonymity). In some embodiments, the ID and/or username are associated with data sets and/or test results.

In some embodiments, subject data sets are produced from the results of a trial (e.g., multiple samples tested by a single subject). In some embodiments, sample data sets are produced from the results on a single sample from multiple subjects. A data set may comprise the map coordinates for responses, time for response, normalized responses (e.g., normalized across the responses for a subject), trial number, subject ID, etc.

In some embodiments, the results of a test performed using the systems, devices and/or methods described herein (e.g., sensory test, test, etc.) analysis are reported (e.g., to a subject, to the test administrator, researcher, principle investigator, etc.). Data (e.g., non-manipulated data) obtained from a subject may be reported as an outcome/result of a test. In other embodiments, data obtained from single subject is analyzed to provide output from interpretation, and it subsequently reported. Data from multiple subjects (e.g., having performed the same test or randomized versions of the same test) may be correlated and then analyzed and/or reported. Data and/or results may be produced by receiving data (e.g., from test of one or more subjects) and/or information (e.g., test samples, expected outcomes, desired outcomes, etc.), transforming the data and/or information and provide an outcome or result (e.g., by comparison to a database, by qualitative assessment, by quantitative assessment, etc.). A result obtained from correlation/analysis of test results may be determinative of an action to be taken (e.g., test different samples (e.g., variations of one or more tested samples), scale up the testing of a particular sample, commercialize a particular sample, etc.). In some embodiments, outcomes from testing by methods described herein are independently verified by further testing (e.g., larger scale testing, other testing strategies, etc.).

In some embodiments, results of testing (e.g., for a particular subject over a range of samples, for a single sample over a range of subjects, for a particular test, for a range of subjects and samples, etc.) are reported (e.g., to a: subject, test administrator, researcher, principle investigator, marketing team, management team, R&D team, etc.). In some embodiments, a result is provided on a peripheral, device, or component of an apparatus. For example, sometimes an outcome is provided by a printer or display. In some embodiments, results are reported in the form of a report. A report may reflect one or bother of quantitative and qualitative interpretation of results. Generally, results are displayed in a suitable format for downstream use/interpretation of the reported information. Non-limiting examples of formats suitable for use for reporting and/or displaying data, results, etc. include text, outline, digital data, a graph, graphs, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, and the like, and combinations of the foregoing.

Generating and reporting results from the tests described herein comprises transformation of subject (e.g., human subject) perceptions (e.g., sensory stimuli) into quantitative data (or representations thereof) that can be used for downstream evaluation of the samples tested. Such a data or representations reflect information not determinable from the individual subject's (or the population's) perception(s) in the absence of the method steps described herein. As such, in some embodiments, the method and systems provided herein address the problem of efficiently and objectively assessing characteristics of a sample (e.g., with reproducible or statistically significant accuracy/precision), particularly when such characteristics require human detection.

In some embodiments, a test administrator, researcher, principle investigator, or any downstream individual, upon receiving or reviewing a report comprising one or more data or results determined from the analyses provided herein, will take specific steps or actions in response. For example, testing of additional samples may be warranted. Production of additional samples may be ordered. Larger scale testing or testing by alternate means for one or more samples may be requested and/or performed. Commercial production of one or more samples may be initiated.

The term "receiving a report" as used herein refers to obtaining, by a communication means, a written and/or graphical representation comprising results or data from testing. The report may be generated by a computer or by human data entry, and can be communicated using electronic means (e.g., over the internet, via computer, via fax, from one network location to another location at the same or different physical sites), or by another method of sending or receiving data (e.g., mail service, courier service and the like). In some embodiments the outcome is transmitted in a suitable medium, including, without limitation, in verbal, document, or file form. Data, analysis, and/or reports may be encrypted to prevent unauthorized viewing. In some embodiments, data analysis, and/or reports are obtainable/viewable by a third party.

As noted above, in some embodiments, systems and method described herein transform data from one form into another form (e.g., subject assessment, population assessment, effect of an ingredient across different samples, effect of a change in ingredients (e.g., addition or an ingredient (e.g., natural or artificial alternative ingredient), etc.), etc. In some embodiments, the terms "transformed", "transformation", and grammatical derivations or equivalents thereof, refer to an alteration of data, e.g., from an initial assessment or set of assessments to a population response or determination regarding an input (e.g., a characteristic description of a sample across a population). In some embodiments, a transformation involves conversion of data comprising multiple assessments from a subject or subjects into a characteristic of a sample in order to solve a problem.

Certain processes and methods described herein (e.g., data acquisition, result analysis, communication, categorizing, database management, etc.) are performed by (or cannot be performed without) a computer, processor, software, module and/or other device. Methods described herein typically are computer-implemented methods, and one or more portions of a method sometimes are performed by one or more processors. In some embodiments, an automated method is embodied in software, processors, peripherals and/or an apparatus comprising the like, that administer or assist in the administration of testing, save data, perform analyses, make database comparisons, provide correlations, etc.

As used herein, software refers to computer readable program instructions that, when executed by a processor, perform computer operations, as described herein.

Apparatuses, devices, systems, software and interfaces may be used to conduct methods described herein. In some embodiments, such hardware and software components allow automation of one or more steps of the methods described herein. Using apparatuses, devices, systems, software and interfaces, a subject or test administrator may, for example, run a test on one or more (e.g., dozens, hundreds) of samples. In some embodiments, through automation, a test administrator may, for example, run a test on one or more (e.g., dozens, hundreds, etc.) of samples and multiple subjects (e.g., dozen, hundreds, etc.).

A system typically comprises one or more devices or apparatus. Each device/apparatus often comprises components selected from memory, processor(s), display, user interface, etc. Where a system includes two or more devices/apparatuses, some or all of the various components of the system may be located at different locations. Where a system includes two or more devices/apparatuses, some or all of the apparatus may be located at the same location as a user (e.g., subject, test administrator, etc), some or all of the apparatus may be located at a location different than a user, all of the apparatus may be located at the same location as the user, and/or all of the apparatus may be located at one or more locations different than the user.

A system may comprise one or more computing apparatuses (e.g., test-performing apparatuses, data analysis apparatus, database-containing apparatus, communication devices, reporting devices, etc.).

A user (e.g., test administrator, subject, etc.) of a device or method herein may, for example, be prompted by software to begin a test. The software/processor may prompt the user to take various steps (e.g., receive sample, score sample, etc.). A programmable processor also may prompt a user to select one or more options based on given parameters. A test administrator, principle investigator, or researcher may be provided (by software/hardware) with options for selecting one or more data feature selections, one or more statistical algorithms, one or more statistical analysis algorithms, one or more statistical significance algorithms, iterative steps, one or more validation algorithms, and one or more graphical representations.

Systems described herein may comprise general components of computer systems, such as, for example, network servers, laptop systems, desktop systems, handheld systems, personal digital assistants, tablets, smart phones, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

System components (e.g., individual testing units, recordation components (e.g. touch screen), etc.) may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user (e.g., subject, test administrator, researcher, principle investigator, etc.) accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory).

In some embodiments, systems described herein comprise or interact with a peripheral and/or component that provides data and/or information. In some embodiments, peripherals and components assist a system in carrying out a function. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a processor, a server, CDs, DVDs, graphic cards, specialized I/O devices (e.g., photo cells, photo multiplier tubes, optical readers, sensors, etc.), one or more flow cells, solid material handling components, fluid handling components, network interface controllers, ROM, RAM, wireless transfer methods and devices (Bluetooth, WiFi, and the like), the world wide web (www), the internet, a computer and/or another module.

The terms "obtaining," "transferring," "receiving," etc. refer to movement of data (e.g., raw test data, processed date, taste signature, correlated data, combined data, population date, etc.) between modules, devices, apparatuses, etc. within a system. These terms may also refer to the handling of samples. Data may be generated in the same location at which it is received, or it may be generated in a different location and transmitted to the receiving location. In some embodiments, data is modified before it is processed (e.g., placed into a format amenable to processing, tabulated, correlated, combined, etc.).

Software may include one or more algorithms in certain embodiments. An algorithm may be used for processing sample, test, combined, and/or stored data; analyzing data; and/or providing results of one or more tests. An algorithm often is a list of defined instructions for completing a task. Starting from an initial state, the instructions may describe a computation that proceeds through a defined series of successive states, eventually terminating in a final ending state. By way of example, and without limitation, an algorithm may be a search algorithm, sorting algorithm, merge algorithm, numerical algorithm, graph algorithm, string algorithm, modeling algorithm, computational geometric algorithm, combinatorial algorithm, machine learning algorithm, cryptography algorithm, data compression algorithm, parsing algorithm and the like. In some embodiments, an algorithm or set of algorithms transform data (e.g., test data) into identifiable results. Algorithms utilized in embodiments herein make improvements in the fields of product design, product optimization, food science, marketing, etc. In certain embodiments, algorithms may be implemented for by software.

In some embodiments, systems and methods described herein solve problems in the design of new products (e.g., edible products), the optimization of products, and/or the alteration of products. Small changes made to a product (e.g., food, beverage, etc.) may make discernible changes to the human-perceived (e.g., consciously, subconsciously, etc.) characteristics of the product. Systems and methods allow researchers, manufacturers, product designers, etc. to assess how those small changes affect human perception of a product. For example, if a first sweetener (e.g., sugar, corn syrup, high fructose corn syrup, stevia, aspartame, sucralose, neotame, acesulfame, saccharin, etc.) in an established product is switched to a second sweetener (or the amount altered)

the systems and methods described herein allow the human perception of that alteration (e.g., on palatability, on taste quality, etc.) to be assessed. Likewise, the effect on various characteristics (e.g., on palatability, on taste quality, etc.) of changes to the amount or type of any ingredient(s) (e.g., fat, salt, oil, spice, flavor, etc.) can be assessed by the systems and methods described herein. In some embodiments, methods and systems described herein find use in altering existing products according to consumer desires. For example, samples of an existing product are created with alteration of a particular ingredient and are tested for desirability to subjects (e.g., taste quality, palatability, etc.).

Example 1

Taste Stimuli can Serve as Reinforcing Stimuli

Experiments were conducted in order to determine if taste stimuli could serve as reinforcing stimuli, that is, if they can modify behavior that produced them. The "efficacy" or "strength" of a reinforcer is defined by the amount of limited resources that are allocated to its procurement. If the cost of procurement is low for a highly efficacious reinforcer, then it will be consumed frequently or in large quantities. As detailed below, a taste consumption game was devised in order to determine the cost a human subject is willing to pay, from a fixed amount of capital provided at the start of the game, to procure more or less of a set of taste stimulus solutions for creating an individualized collection of the taste solutions that are most appetitive to (or best "like" by) the subject. The value assigned to each taste stimulus solution through the actions of the subject during the game was tested for its ability to predict the likelihood of future consumption if the subject was given free access to the solutions.

Figure 6A:
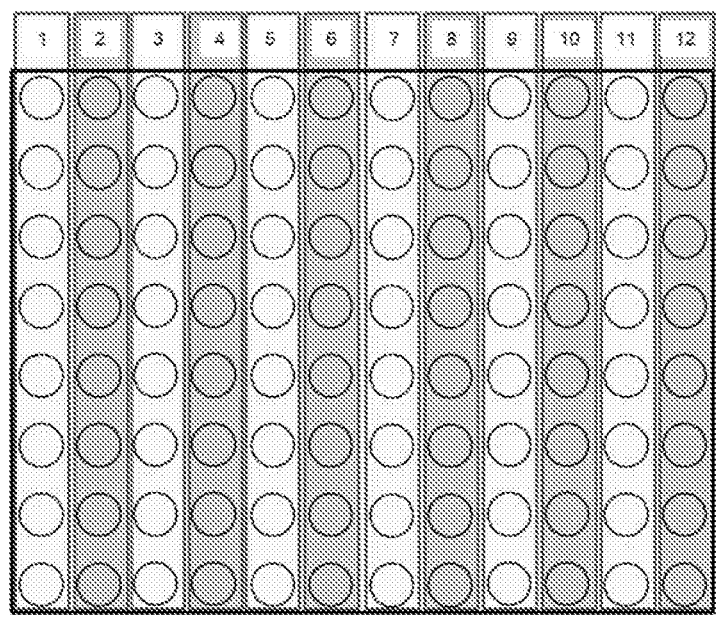
FIG. 6 (A) shows three sets of 11 taste stimulus solutions created from various concentrations of citric acid, glutamic acid, quinine, NaCl, sucrose, rebaudioside A, or mixtures of these used in Example 1. Each solution of a set was dispensed in 8 wells of a 96-well plate according the general configuration shown in the figure. In each plate, 8 wells also were designated for water.
As shown in FIG. 6(B), the resulting plates were labeled "A," "B," and "C."

Materials and methods. Citric acid, NaCl, quinine, glutamic acid, sucrose, and rebaudioside A were dissolved in water at concentrations indicated in figure captions to give a total of 12 solutions per test. Each solution was dispensed in 8 wells of 96-well plate (8 rows×12 columns; See FIG. 6). The 96-well plate was then placed on an x-y motion table of a TaStation®, Opertech Bio, Inc., Philadelphia, PA, USA, apparatus. The x-y motion table was moved in a randomized pattern by the TaStation® algorithm so that a single well of the 96-well plate aligned to the tip of an electronic pipette mounted directly above on a z-axis gantry. At the start of a trial, the pipette was automatically lowered into the well and 200 μl of solution were drawn by the pipette. The pipette then was moved vertically to a position ready for the subject to grasp and remove.

Figure 7:
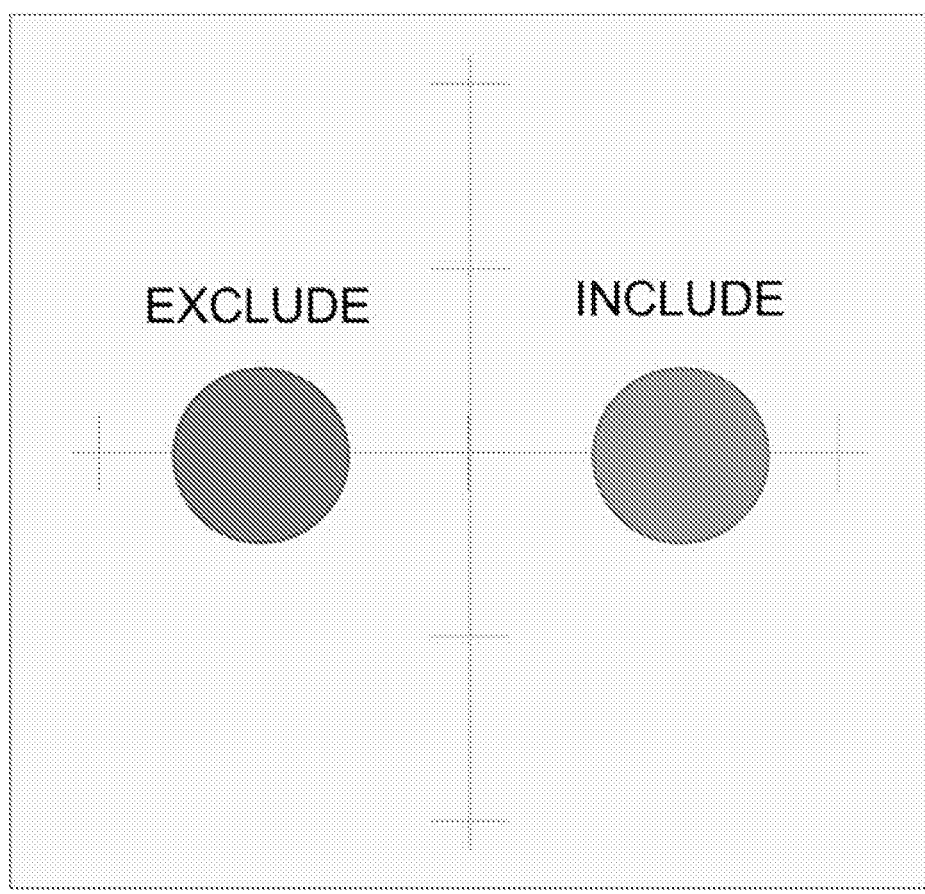
FIG. 7 shows the display appearing on a touch sensitive monitor that upon which, after tasting, the subject made a decision on including or excluding the sample just tasted from the plate that was created through successive trials of the session.
Figure 8A:
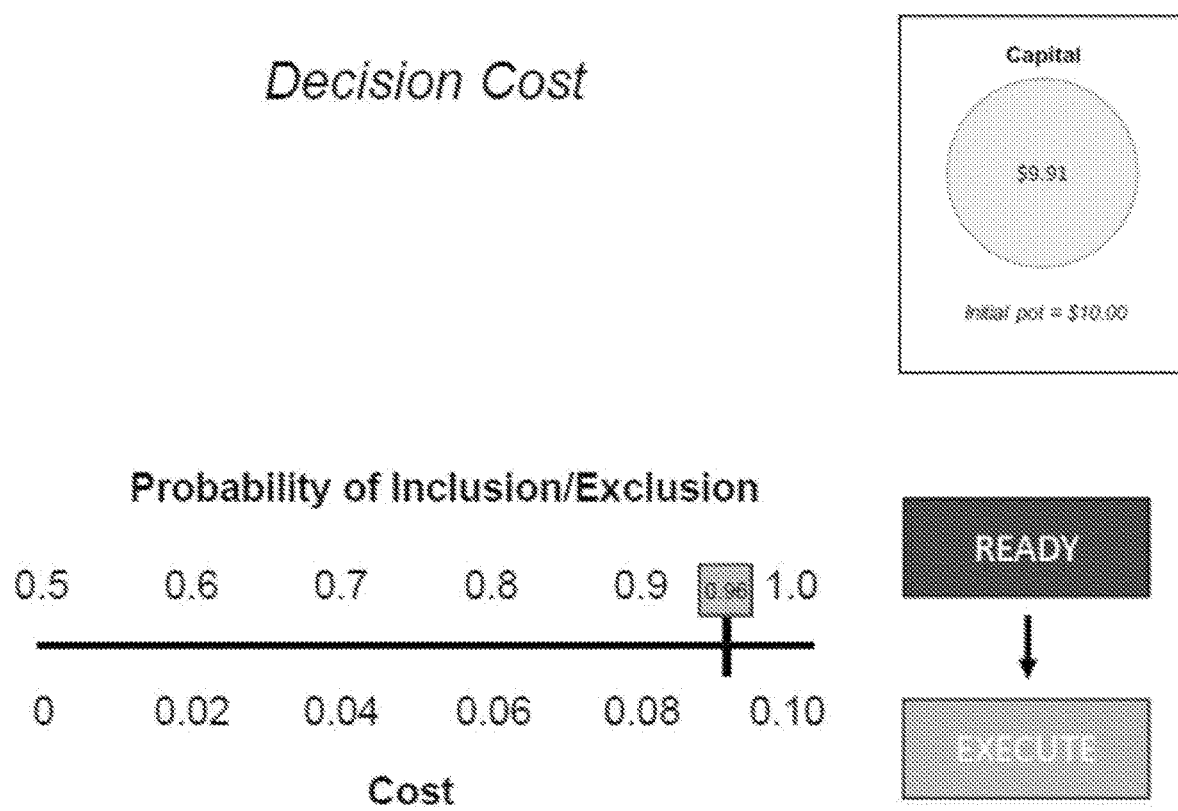
FIG. 8A shows a bar displayed on the monitor that a subject can move to place the probability of inclusion/exclusion (previous choice). The bar indicates the probability to nearest $100^{th}$. Capital available to the subject (also indicated on the monitor) is adjusted as the bar is moved.

Subjects followed a series of prompts on a touch-sensitive computer monitor to guide them step-by-step through the entire process of tasting and recording a response. Prompted by the first command, subjects removed the loaded pipette from the ready position and then self-administered the solution to their tongue by operating the pipette. Upon replacing the pipette to the mount on the z-axis gantry, a visual display appeared on the touch-sensitive monitor that presented a choice of action between "include" or "exclude" (See FIG. 7). Subjects then selected the choice of action by touching the appropriate target displayed on the screen. Upon selecting the choice of action, a new display appeared on the monitor which included an image depicting the "pot" or capital amount given to the subject at the start of the game (SEE FIG. 8A, inset upper right corner). The "pot" was an account provided to the subject from which to spend on each action of inclusion or exclusion. Also appearing on the screen was a sliding bar on a scale that depicted a monetary value (ranging from $0.00 to $0.10) on one side and a probability (ranging from 0.0 to 1.0) on the other side of the scale (See FIG. 8A).

The subject moved the bar to a monetary value (and corresponding probability) that was dependent on the degree to which the subject desired a particular outcome. Once the value/probability was selected, the subject pressed a button next to the sliding scale labeled "EXECUTE" to execute the choice of action from the previous display. Immediately upon pressing "EXECUTE," the amount of the money selected on the monetary scale was subtracted from the subject's "pot," and the amount of remaining capital was adjusted and displayed. Thus, there was a cost to execute the choice of action for each trial, and the cost paid was assumed to directly reflect the subject's desire to carry out the inclusion/exclusion command. The subject could pay the maximum allowed for a trial (in this case, $0.10) to guarantee (i.e., probability=1.0) that the sample would be included in (if highly appetitive) or excluded from (highly aversive) the plate they were creating. An expenditure of $0.00 resulted in execution of a choice of action with a probability of 0.5 (random) and thus was an indication of indifference toward the sample. Expenditures ranging in-between the extremes corresponded to increasing probabilities that the choice of action would be carried out as desired. Pressing the "EXECUTE" button completed a trial, and automatically set the apparatus and algorithm into operation for the next trial. No inter-trial interval was specified; each subject was allowed to take as much time as desired. All subjects completed their test sessions (i.e., all 96 trials, one trial per each well of the 96-well plate) in approximately 45 minutes.

Figure 8B:
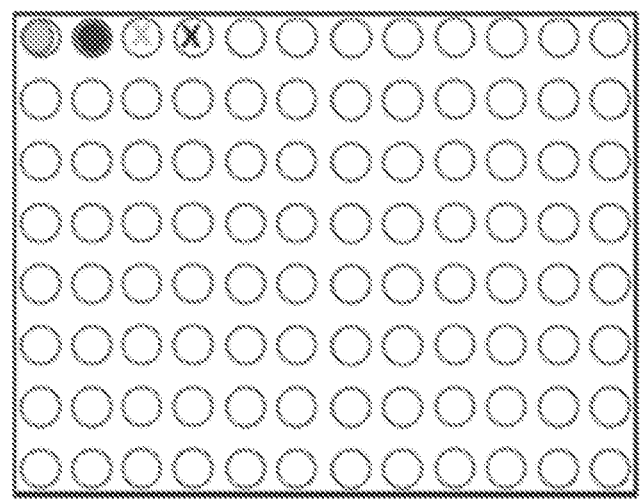
FIG. 8B shows a grid continuously displayed on the monitor that kept track of actions and outcomes as the subject progressed through each trial. A colored chip or "X" progressively appeared in the wells as each trial concluded; a chip indicated inclusion, an x indicated exclusion from the plate; colors may be used to indicate a desired outcome (grey), whereas other color used to indicate the undesired outcome (black).

Also appearing on the touch-sensitive monitor continuously throughout the game session was an 8×12 grid that provided visual feedback to the subject on the progress on their plate's creation as the test session advanced, updating on each trial the outcome of the subject's action (See FIG. 8B). The occurrence of a chip in a well of the grid indicated that a sample was included as the outcome of that trial, whereas an "X" indicated that the sample had been excluded. The color of the chip or "X" indicated whether the outcome was desired or not—grey indicated that the desired choice of action had been carried out, and black indicated the contrary.

Upon completion of the test session (i.e., actions have been executed on all 96 trials) the subject's created plate was automatically entered into a virtual (computer-generated) market that judged and consequently placed a monetary value on the quality of the plate and returned a monetary reward to the subject for the plate's design. The market value was displayed on the monitor. This step was necessary to incentivize the investment of capital by the subject (withdrawn from the subject's "pot") in the creation of the plate. Immediately after the display of the market value, the subject was compensated with actual money equal to the remaining sum in the subject's "pot" plus the market value. Thus the expenditures of capital from the "pot" signify real values (i.e., not purely conceptual in the context of a game) to the subject, because the contents of the "pot" represent actual currency that is paid to the subject at the game's conclusion. Since amount of money spent provides an indication of reinforcing efficacy, and reinforcing efficacy provides an indication of consumption, the expenditures made by the subject on each item in the plate's creation indicate and/or can be used to determine and/or quantify the subject's consumption (e.g., the subject's pattern of consumption and/or the likelihood of the subject to consume) under conditions of free access.

The Virtual Market can be created by a variety of methods, all of which are designed to provide an incentive to the subject for spending the money in their "pot" (i.e., investing their capital) to create their plate of most "liked" taste stimulus solutions without providing feedback that could shape the subject's future selections (if he or she were to participate in multiple sessions.)

As configured, the incentive guarantees, on average, a return from the virtual market that exceeds the total spent by the subject for the plate creation. For example, if the subject has spent $9.00, he or she must recover the $9.00 investment, plus an extra profit, from the virtual market. However, as described herein, other configurations are possible.

The method by which the virtual market determines a value for the subject's plate is not made known or ascertainable by the subject, or else the subject will attempt to use that information to guide the design of the plate composition. Thus, if the subject learns how to "game" the market, the plate contents will not reflect the subject's personal "likes" and "dislikes" among the test solutions, but instead will reflect the subject's anticipation of what will bring the highest return from the market. To accomplish a guaranteed profit while disguising the market's methods, a random selection of market strategies can be applied that results in the profit.

In alternative embodiments, a virtual market strategy can be realized through game theory resulting in a Nash equilibrium, a condition under which knowledge of the virtual market strategy would not impact the subject's choices made in the creation of his or her plate.

Among the simplest methods used to generate the virtual market reward was to multiply the amount spent by the subject in the creation of the plate by a randomly generated number from the interval of 1 to 15. That product equated to the virtual market awarded to the subject. The virtual market value thus generated was added to the remaining sum in the subject's "pot," and the grand total was paid in actual currency ($) to the subject at the completion of the session.

As detailed and described herein, subject performance in test plate creation may be optimized by through a variety of virtual market strategies.

Example 2

Test for Consumption under Condition of Free Access

The solutions described in Example 1 were dispensed as 30 ml volumes each in three of 36 plastic cups. The filled cups then were arranged in a randomized order on a table top. The subject was given a small paper straw to draw by mouth the solutions from the cups. At the start of the session, the subject was handed the first cup from the arrangement and instructed to drink through the straw as much of the 30 ml as desired within 10 seconds (the 10-second timer was started when the subject had securely grasped the cup.) When the subject was finished drinking from the sample, the subject returned the cup, thereby completing the trial. Each successive trial began when the subject indicated that they were ready (there was no set inter-trial interval). All subjects completed the task of drinking from all 36 cups in 15 minutes or less.

Two sets of data, shown in FIGS. 9-12, are each from two individual subjects using "Plate A" (See FIG. 6), are presented to compare results from the TāStation® consumption model game to those from a test of free consumption (using the same solutions used for "Plate A").

In both cases, the results from the TāStation® game corresponded to those obtained from the free consumption test, with relatively higher prices paid for those solutions that subsequently either were consumed the most (e.g., higher concentrations of sucrose) or least (e.g., quine solutions) in the free access consumption test, and the least amount paid for intermediately consumed solutions (e.g., water, NaCl, low sucrose concentrations). Adding quinine to 200 mM sucrose decreased both the price paid for inclusion and the amount consumed in a concentration-dependent manner.

Although the overall pattern of spending was similar between Subject ME and Subject SN, ME paid higher absolute prices for inclusion of sucrose solutions than did SN (See FIG. 9A vs FIG. 11A). Nevertheless, both ME and SN consumed similar volumes of sucrose solutions (See FIGS. 9B and 11B), following patterns that were reflective of their relative spending. The data indicates that the overall pattern of relative spending, rather than absolute amounts spent, indicate and/or predict future consumption under the conditions defined by these experiments.

Figure 10:
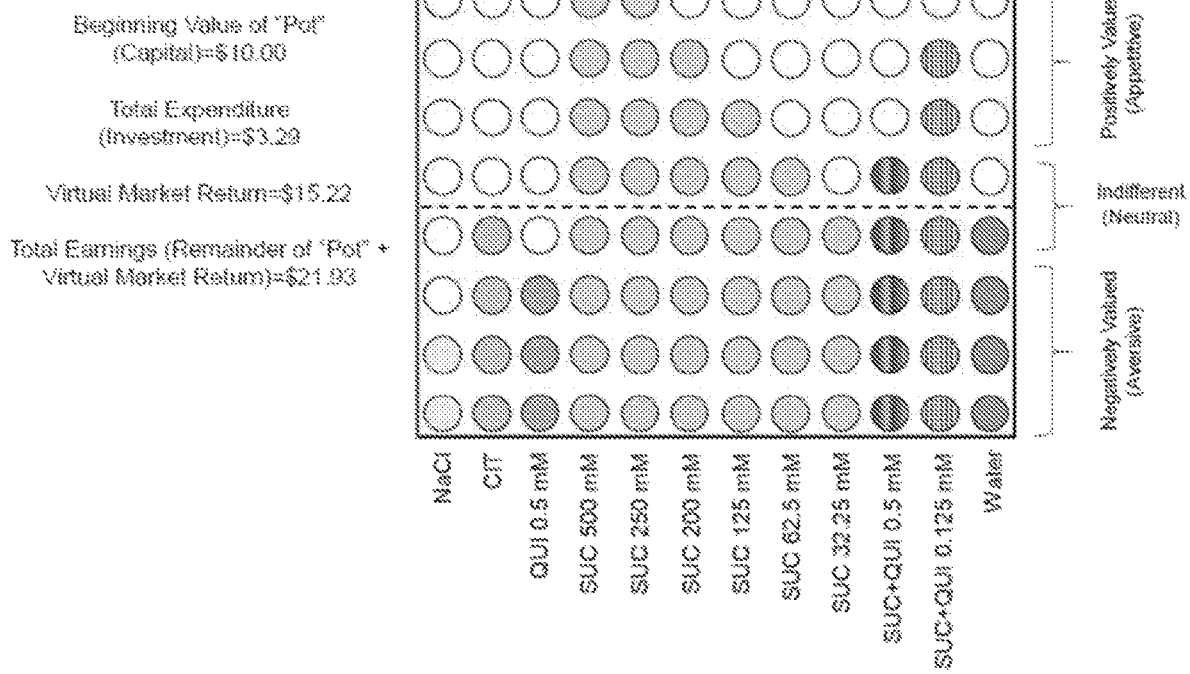
FIG. 10 shows final plate created by Subject ME from the TāStation® consumption model game. Colored wells indicate the presence of a taste stimulus solution; wells with no color indicate empty wells. The occupancy of a well was determined probabilistically by the computer algorithm using the monetary value and corresponding probability of choice-execution set by the subject on each trial. Starting value of the subject's pot was $10.00, and the cumulative amount spent by the subject in the plate's creation was $3.29. The Virtual Market returned a value of $15.22, and that value was added to the remaining sum in the subject's "pot" for total earnings of $21.93 (paid to the subject in actual currency at the completion of the session).
Figure 11:
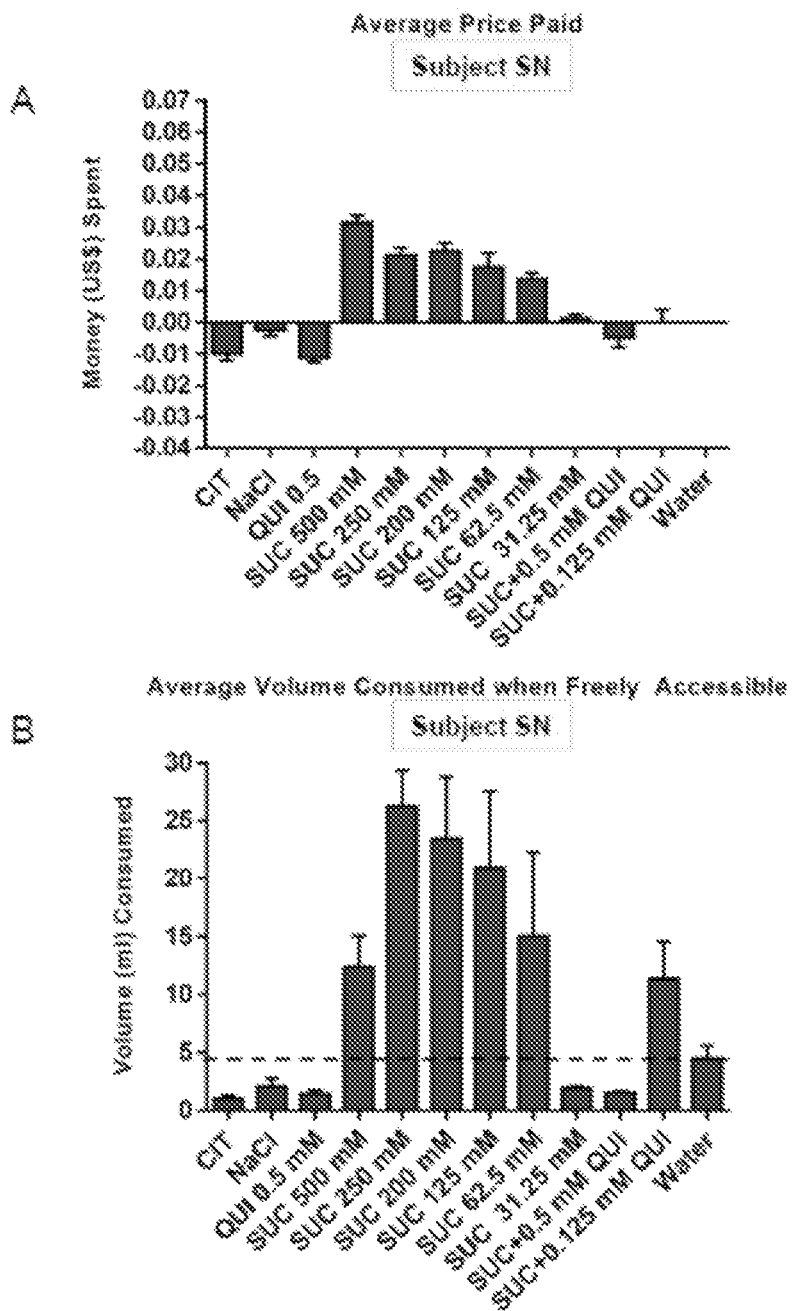
FIG. 11 shows (A) Price paid on each trial of a given sample to execute the action of "include" or "exclude" in the creation of a customized plate of taste stimulus solutions most "liked" by Subject SN using the TāStation® consumption model game; each of 12 solutions ("Plate A," described in FIG. 6) was presented automatically and randomly in replicates of 8. Positive values on the ordinate indicate the absolute amounts of money spent for inclusion, whereas negative values indicate the absolute amounts of money spent for exclusion. (B) Average volumes (out of 30 ml per sample) consumed through a straw by Subject SN when given free access to the samples randomly presented in plastic cups; each of the 12 "Plate A" solutions was dispensed in 3 cups (i.e., total of 36 samples); the cups were given to the subject in a randomized order. The dashed line highlights the average volume per sample of water consumed. CIT=citric acid (10 mM), NaCl=sodium chloride (100 mM), QUI=quinine, SUC=sucrose. Data shown in (A) and (B) were collected on separate days.
Figure 12:
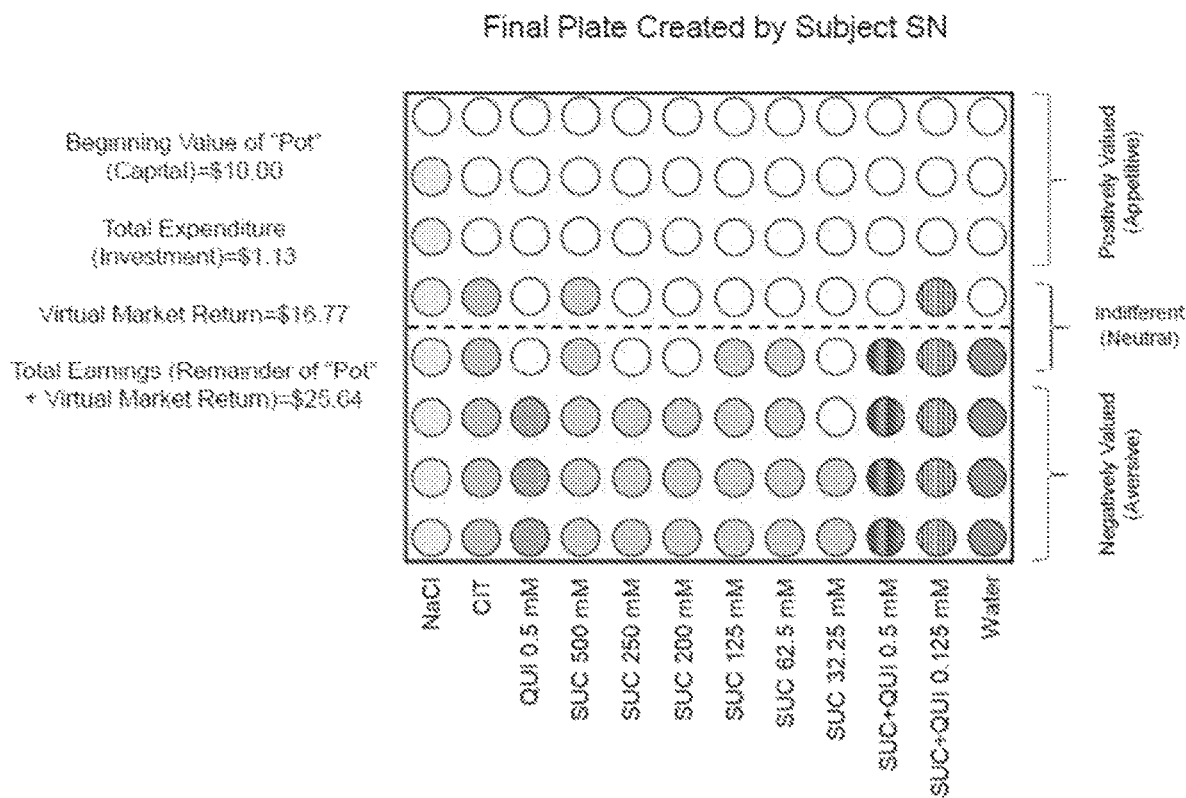
FIG. 12 shows final plate created by Subject SN from the TāStation® consumption model game. Colored wells indicate the presence of a taste stimulus solution; wells with no color indicate empty wells. The occupancy of a well was determined probabilistically by the computer algorithm using the monetary value and corresponding probability of choice-execution set by the subject on each trial. Starting value of the subject's pot was $10.00, and the cumulative amount spent by the subject in the plate's creation was $1.13. The Virtual Market returned a value of $16.77, and that value was added to the remaining sum in the subject's "pot" for total earnings of $25.64 (paid to the subject in actual currency at the completion of the session).

Since the amounts spent per trial by the subject determined the probability of inclusion or exclusion, greater expenditures resulted in more representation of positively valued solutions, and less representation by negatively valued solutions, in the subject's created plate (See FIGS. 10 and 12). Subject ME spent more on the plate creation than did Subject SN, and consequently greater variation in representation of the taste stimulus solutions resulted in ME's plate (See FIG. 10) compared to SN's plate (FIG. 12).

It is conceivable that Subject SN invested less of the capital provided in the "pot" because of inherent "risk aversion;" in other words, SN may have placed higher value on the certainty of the "pot" than on the potential for reward returned by the virtual market. In such a case, the "risk aversion" potentially may be overcome by adjusting variables in the algorithm such as the starting amount provided in the "pot," the limits on expenditures, and the virtual market strategy (if the subject participates in multiple sessions.)

Alternatively, Subject SN might not have been sufficiently familiar with the concepts of probability to effectively translate desired choice-execution to actual outcome in the game. In such a case, the TāStation® consumption model game could be used to teach concepts of probability, or other mathematical concepts, to a subject.

Unexpected result: In the TāStation®-generated datasets, a departure from the concentration-dependence of the apparent price-consumption relationship is evident at the highest concentration (500 mM) of sucrose. Both subjects paid their highest price for 500 mM sucrose (approximately $0.06 per trial for Subject ME, and approximately $0.02 per trial), yet consumed lesser volumes of this concentration in the free access consumption test than of lower concentrations for which the subjects paid less money. Such a result indicates the existence of additional non-obvious variables that are relevant to the measure of reinforcing efficacy. For example, it is possible that physical properties specific to 500 mM sucrose, such as viscosity, compete with taste to impact the rate of consumption. It is furthermore possible that the reinforcing efficacy of 500 mM sucrose is sufficiently great (reflected in the price paid by the subjects) that motivation to consume it rapidly saturates (as might be the case for highly palatable foods such as chocolate truffles.)

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method of identifying taste preference comprising:
   (a) providing a taste sample to a human subject via an automated robotic arm and pipette;
   (b) recording in memory, by a processor, the subject's response to the taste sample on a touch screen, wherein the response comprises
      (i) the subject's decision to include or exclude the taste sample from a plate of retained samples; and
      (ii) a weighted value, determined by the subject, that is associated with the decision to include or exclude the taste sample from the plate of retained samples;
   wherein the subject is provided an initial sum of goods to be used for providing the weighted value associated with the decision to include or exclude; and wherein the touch screen presents the subject with a means for identifying the weighted value of the initial sum of goods with the decision to include or exclude the taste sample from the plate of retained samples; and
   (c) reducing, by the processor, the initial sum of goods by the weighted value;
   (d) repeating steps (a)-(c) with additional taste samples until all taste samples within a population of taste samples have been provided and the subject's response recorded;
   (e) determining, by the processor, the taste samples from the population of taste samples included in the plate of retained samples based probabilistically on the recorded weighted values;
   (f) comparing, by the processor, the taste samples present in the plate of retained samples to a control or another subject's results; and
   (g) rewarding the subject based upon the comparison.

2. The method of claim 1, wherein the initial sum of goods is an initial sum of money.

3. The method of claim 1, wherein the initial sum of goods is an initial sum of money; and wherein the means comprises a sliding scale that monetizes based on probability the likelihood of including or excluding the sample.

4. The method of claim 1, wherein rewarding the subject comprises compensating the subject based upon how many samples present in the subject's plate of retained samples are common to a cumulative set of samples that are present in the plates of other subjects that generated a plate of retained samples using the same population of taste samples being tested.

5. The method of claim 1, wherein rewarding the subject based upon the taste samples present in the plate of retained samples comprises a direct payment made to a subject that compensates the subject for loss due to expenditures.

6. The method of claim 1, wherein rewarding the subject based upon the taste samples present in the plate of retained samples comprises a direct payment made to a subject that results in a net profit to the subject in an amount that exceeds the sum of expenditures.

7. The method of claim 1, wherein rewarding the subject based upon the taste samples present in the plate of retained samples comprises a reward that is based on consistency of a subject's value assessment with information obtained from a database of values assessed for commodities is used.

8. The method of claim 7, wherein the database is populated by results of repeated tests of each of the commodities.

9. The method of claim 7, wherein rewarding the subject based upon the taste samples present in the plate of retained samples comprises use of a Virtual Market to reward the subject.

10. The method of claim 9, wherein the Virtual Market provides a fixed or randomly generated sum to the amount spent by the subject in a plate creation step, multiplies the sum spent by the subject in a plate creation step by a fixed or by a randomly generated variable, or combines both an additive and multiplicative value to the amount spent by the subject in a plate creation step.

11. A method for taste preference analysis comprising:
   providing a population of taste samples present in a plate;
   selecting individual taste samples from the plate and presenting the individual taste samples with a robotic arm and pipette to a subject;
   prompting the subject on a display to make a determination to include or exclude the presented individual taste sample from a plate of retained samples;
   providing a cost of execution presentation on the display to the subject that the subject adjusts to scale associating the cost of executing the determination to include or exclude with the probability of outcome for the choice; wherein the subject is provided an initial sum of goods to be used for the cost of executing the decision to include or exclude;
   recording in memory, by a processor, the subject's decision to include or exclude and the scaled cost of executing;
   reducing, by the processor, the initial sum of goods by the scaled cost of executing;
   determining, by the processor, the plate of retained samples based probabilistically on the recorded decisions of the subject;
   comparing, by the processor, the plate of retained samples to taste samples present in a different subject's plate of retained samples; and
   rewarding the subject based upon the similarity of the taste samples present in the subject's plate of retained samples compared to the samples present in a different subject's plate of retained samples.

* * * * *